US008450071B2

(12) United States Patent
Pereira

(10) Patent No.: US 8,450,071 B2
(45) Date of Patent: May 28, 2013

(54) BIOMARKER AND METHOD FOR DETECTING A CHRONIC INFLAMMATORY-ASSOCIATED DISEASE

(75) Inventor: Heloise Anne Pereira, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 12/904,917

(22) Filed: Oct. 14, 2010

(65) Prior Publication Data

US 2011/0250623 A1    Oct. 13, 2011

Related U.S. Application Data

(63) Continuation-in-part of application No. 12/697,906, filed on Feb. 1, 2010, now abandoned, which is a continuation of application No. 11/712,028, filed on Feb. 28, 2007, now Pat. No. 7,655,480, which is a continuation-in-part of application No. 10/384,474, filed on Mar. 7, 2003, now abandoned.

(60) Provisional application No. 60/363,114, filed on Mar. 8, 2002.

(51) Int. Cl.
*G01N 33/53* (2006.01)

(52) U.S. Cl.
CPC ............. *G01N 33/53* (2013.01); *Y10S 436/811* (2013.01)
USPC ............ 435/7.1; 435/7.92; 436/501; 436/811

(58) Field of Classification Search
None
See application file for complete search history.

(56) References Cited

U.S. PATENT DOCUMENTS

| 7,655,480 B2 | 2/2010 | Pereira |
| 2003/0139353 A1 | 7/2003 | Jackson et al. |
| 2003/0157580 A1 | 8/2003 | Hochstrasser et al. |
| 2003/0158083 A1 | 8/2003 | Peters |
| 2010/0136574 A1 | 6/2010 | Pereira |
| 2011/0250623 A1 | 10/2011 | Pereira |

FOREIGN PATENT DOCUMENTS

WO  PCT/US2011/056331    2/2012

OTHER PUBLICATIONS

Strongin, Laboratory Diagnosis of Viral Infections, Sensitivity, Specificity, and Predictive Value of Diagnostic Tests: Definitions and Clinical Applications, Lennette, e., ed., Marcel Dekker, Inc., New York, pp. 211-219, 1992.*
Pereira., Novel isoform of CAP37 Expressed in Endothelial Cells and Localized to Atherosclerotic Lessions, Ofice of Technology Development, The University of Oklahoma, Oct. 2011 (abstract only).*
Linder et al., Roles of Heparin-Binding Protein in Bacterial Infections, Journal of Innate Immunity, 2010; 2; pp. 431-438.*

Akiyama H. et al.: Inflammation and Alzheimer's disease. Neurobiol of Aging (Jan. 17, 2000), vol. 21, pp. 383-421.
Brackett D.J. et al.: A synthetic lipopolysaccharide-binding peptide based on the neutrophil-derived protein CAP37 prevents endotoxin-induced responses in conscious rats. Infect Immun (1997), vol. 65, pp. 2803-2811.
Chomczynski P. et al.: Single-step method of RNA isolation by acid guanidinium thiocyanate-phenol-chloroform extraction. Anal Biochem (1987), vol. 162, pp. 156-159.
Corpet F.: Multiple sequence alignment with hierarchical clustering. Nucl Acids Res (1988), vol. 16, pp. 10881-10890.
Diglio C.A. et al.: Angiogenesis in rat aorta ring explant cultures. Lab Invest (1989), vol. 60, pp. 523-531.
Enk C.D. et al: UVB induces IL-12 transcription in human keratinocytes in vivo and in vitro. Photochem Photobio (1996), vol. 63, pp. 854-859.
Flodgaard H. et al.: Covalent structure of two novel neutrophile leucocyte-derived proteins of porcine and human origin: neutrophil elastase homologues with strong monocyte and fibroblast chemotactic activities. Eur J Biochem (1991), vol. 197, pp. 535-547.
Gautam N. et al.: Heparin-binding protein (HBP/CAP37): A missing link in neutrophil-evoked alteration of vascular permeability. Nat Med (2001), vol. 7, pp. 1123-1127.
Gräbner R. et al.: Flow cytometric determination of E-selectin, vascular cell adhesion molecule-1, and intercellular cell adhesion molecule-1 in formaldehyde-fixed endothelial monolayers. Cytometry (2000), vol. 40, pp. 238-244.
Grammas P.: A damaged microcirculation contributes to neuronal cell death in Alzheimer's disease. Neurobiol Aging (2000), vol. 21, pp. 199-205.
Heinzelmann M. et al.: Endocytosis of heparin-binding protein (CAP37) is essential for the enhancement of lipopolysaccharide-induced TNF-α production in human monocytes. J Immunol (1999), vol. 162, pp. 4240-4245.
Heinzelmann M. et al.: Heparin-binding protein (CAP37) is internalized in monocytes and increases LPS-induced monocyte activation. J Immunol (1998), vol. 160, pp. 5530-5536.
Jaffe A.E. et al.: Culture of human endothelial cells derived from umbilical veins. J Clin Invest (1973), vol. 52, pp. 2745-2756.
Kahn et al.: Contact-system activation in children with vasculitis, The Lancet, vol. 360 (Aug. 17, 2002), pp. 535-541.

(Continued)

*Primary Examiner* — Gary W Counts
(74) *Attorney, Agent, or Firm* — Dunlap Codding, P.C.

(57) ABSTRACT

The present invention in one embodiment uses detection of isoforms of CAP37 as an early detection marker for a chronic inflammatory-associated disease. Chronic inflammatory-related diseases may include, for example, atherosclerosis, psoriasis, and osteoarthritis. The invention is also directed to isoforms of CAP37 protein having apparent molecular weights of about 135 kDa (±15 kDa) and about 100 kDa (±15 kDa) as assessed by SDS PAGE under reducing conditions, and their use as biomarkers for the presence of a chronic inflammatory-associated disease in a subject. The invention is also directed to monoclonal and/or polyclonal antibodies raised against such isoforms of CAP37 protein and kits and diagnostic tests comprising these antibodies.

7 Claims, 24 Drawing Sheets

OTHER PUBLICATIONS

Lee et al.: Demonstration of CAP37, a monocyte chemoattractant in endothelial cells, FASEB Journal (Mar. 7, 2001), vol. 15, No. 4, pp. A393.

Lee T.D. et al.: CAP37, a Novel Inflammatory Mediator Its Expression in Endothelial Cells and Localization to Atherosclerotic Lesions. American Journal of Pathology, vol. 160, No. 3, (Mar. 2002), pp. 841-848.

Lonnemann G. et al.: Differences in the synthesis and kinetics of release of interleukin 1 alpha, interleukin 1 beta and tumor necrosis factor from human mononuclear cells. Eur J Immunol (1989), vol. 19, pp. 1531-1536.

Morgan J.G. et al.: Cloning of the cDNA for the serine protease homolog CAP37/Azurocidin, a microbicidal and chemotactic protein from human granulocytes. J Immunol (1991), vol. 147, pp. 3210-3214.

McGeer et al., "Activation of the classical complement pathway in brain tissue of Alzheimer patients", Neuroscience Letters, vol. 107 (May 17, 1989) pp. 341-346.

McGeer et al., "Inflammation in the Brain in Alzheimer's Disease:Implications for Therapy", Neuroscience News, vol. 1, No. 2, (No Month, 1998) pp. 29-35.

Olofsson A.M. et al.: Heparin-binding protein targeted to mitochondrial compartments protects endothelial cells from apoptosis. J Clin Invest (1999), vol. 104, pp. 885-894.

Østergaard E. et al.: A neutrophil-derived proteolytic inactive elastase homologue (hHBP) mediates reversible contraction of fibroblasts and endothelial cell monolayers and stimulates monocyte survival and thrombospondin secretion. J Leukoc Biol (1992), vol. 51, pp. 316-323.

Pereira H.A. et al.: CAP37, a 37kD human neutrophil granule cationic protein shares homology with inflammatory proteinases. Life Sciences (1990), vol. 46, pp. 189-196.

Pereira H.A.: Cationic Antimicrobial proteing of Mr 37 kDa: a multifunctional inflammatory protein. Chines Medical Journal (2001), vol. 114(1), pp. 9-13.

Pereira H.A. et al.: CAP37, a human neutrophil-derived chemotactic factor with monocyte specific activity. J Clin Invest (1990), vol. 85, pp. 1468-1476.

Pereira H.A. et al.: CAP37, a neutrophil granule-derived protein stimulates protein kinase C activity in endothelial cells. J Leukoc Biol (1996), vol. 60, pp. 415-422.

Pereira H.A. et al.: Expression of CAP37, a novel inflammatory mediator, in Alzheimer's disease. Neurobiol Aging (1996), vol. 17, pp. 753-759.

Pereira H.A. et al.: Synthetic bactericidal peptide based on CAP37: a 37-kDa human neutrophil granule-associated cationic antimicrobial protein chemotactic for monocytes. Proc Natl Acad Sci (USA) (1993), vol. 90, pp. 4733-4737.

Pereira H.A.. et al.: Quantitation of a cationic antimicrobial granule protein of human polymorphonuclear leukocyts by Elisa. J. Immunol. Meth., (1989), vol. 117, pp. 115-120.

Pereira et al., "CAP37, an inflammatory mediator in Alzheimer's disease", The FASEB Journal, vol. 22, No. 1, 67.11 (2008) (abstract).

Pohl J.. et al.: Amino acid sequence of CAP37, a human neutrophil granule-derived antibacterial and monocyte-specific chemotactic glycoprotein structurally similar to neutrophil elastase. FEBS Letters (1990), vol. 272, pp. 200-204.

Rasmussen P.B. et al.: Characterization of recombinant human HBP/CAP37/azurocidin, a pleiotropic mediator of inflammation-enhancing LPS-induced cytokine release from monocytes. FEBS letters (1996), vol. 390, pp. 109-112.

Reining et al.: Cap37 During Cardiopulmonary Bypass, Increase in Plasma Levels Upon Heparin and LMWH, Abstracts of the 16th Annual Congress of the ESICM, Poster Session, Acute Lung Injury, Amsterdam, Netherlands (Oct. 5-8, 2003), p. S87.

Ross R.: Atherosclerosis—an inflammatory disease. N Engl J Med (1999), vol. 340, pp. 115-126.

Sears P. et al.: Enzyme action in glycoprotein synthesis. Cell Mol Life Sci (1998), vol. 54, pp. 223-252.

Shafer W.M. et al.: Cationic antimicrobial proteins isolated from human neutrophil granulocytes in the presence of diisopropyl fluorophosphate. Infect Immun (1984), vol. 45, pp. 29-35.

Shafer W.M. et al.: Late intraphagosomal hydrogen ion concentration favors the in vitro antimicrobial capacity of a 37-kilodalton cationic granule protein of human neutrophil granules. Infect Immun (1986), vol. 53, pp. 651-655.

Strongin: Laboratory Diagnosis of Viral Invections, Sensitivity, Specificity, and Predictive Value of Diagnostic Tests: Definintions and Clinical Applicatins, Lennette, ed. Marcel Dekker, Inc. New York (1992), pp. 211-219.

Tapper et al.: Secretion of heparin-binding protein from human neutrophils is determined by its localization in azurophilic granules and secretory vesicles, Blood, (Mar. 1, 2002), vol. 99, No. 5, pp. 1785-1793.

Walter M.J. et al.: Interleukin 12 p40 production by barrier epithelial cells during airway inflammation. J Exp Med (2001), vol. 193, pp. 339-351.

Pereira, "Early Detection Marker for Chronic Inflammatory Associated Disease" U.S. Appl. No. 10/384,474, filed Mar. 7, 2003, Office Action Election/Restriction, mailed Jan. 26, 2006, 5 pgs.

Pereira, "Early Detection Marker for Chronic Inflammatory Associated Disease" U.S. Appl. No. 10/384,474, filed Mar. 7, 2003, Response to Election Requirement, mailed Feb. 7, 2006, 5 pgs.

Pereira, "Early Detection Marker for Chronic Inflammatory Associated Disease" U.S. Appl. No. 10/384,474, filed Mar. 7, 2003, Office Action, mailed Apr. 18, 2006, 13 pgs.

Pereira, "Early Detection Marker for Chronic Inflammatory Associated Disease" U.S. Appl. No. 10/384,474, filed Mar. 7, 2003, Amendment and Response, mailed Jun. 5, 2006, 11 pgs.

Pereira, "Early Detection Marker for Chronic Inflammatory Associated Disease" U.S. Appl. No. 10/384,474, filed Mar. 7, 2003, Office Action, mailed Aug. 28, 2006, 10 pgs.

Pereira, "Method for Predicting Sepsis or an Acute Infectious Inflammatory Response" U.S. Appl. No. 11/712,028, filed Feb. 28, 2007, Office Action Election/Restriction, mailed Oct. 31, 2007, 6 pgs.

Pereira, "Method for Predicting Sepsis or an Acute Infectious Inflammatory Response" U.S. Appl. No. 11/712,028, filed Feb. 28, 2007, Response to Restriction Requirement, mailed Nov. 15, 2007, 2 pgs.

Pereira, "Method for Predicting Sepsis or an Acute Infectious Inflammatory Response" U.S. Appl. No. 11/712,028, filed Feb. 28, 2007, Office Action, mailed Dec. 27, 2007, 6 pgs.

Pereira, "Method for Predicting Sepsis or an Acute Infectious Inflammatory Response" U.S. Appl. No. 11/712,028, filed Feb. 28, 2007, Amendment, mailed Mar. 26, 2008, 5 pgs.

Pereira, "Method for Predicting Sepsis or an Acute Infectious Inflammatory Response" U.S. Appl. No. 11/712,028, filed Feb. 28, 2007, Final Office Action, mailed Jun. 23, 2008, 7 pgs.

Pereira, "Method for Predicting Sepsis or an Acute Infectious Inflammatory Response" U.S. Appl. No. 11/712,028, filed Feb. 28, 2007, Request for Continued Examination and Amendment and Response, mailed Nov. 10, 2008, 11 pgs.

Pereira, "Method for Predicting Sepsis or an Acute Infectious Inflammatory Response" U.S. Appl. No. 11/712,028, filed Feb. 28, 2007, Office Action, mailed Dec. 15, 2008, 10 pgs.

Pereira, "Method for Predicting Sepsis or an Acute Infectious Inflammatory Response" U.S. Appl. No. 11/712,028, filed Feb. 28, 2007, Amendment and Response, mailed Jun. 10, 2009, 9 pgs.

Pereira, "Method for Predicting Sepsis or an Acute Infectious Inflammatory Response" U.S. Appl. No. 11/712,028, filed Feb. 28, 2007, Declaration of H. Anne Pereira, Ph.D. Under 37 CFR 1.132, mailed Jun. 10, 2009 6 pgs.

Pereira, "Method for Predicting Sepsis or an Acute Infectious Inflammatory Response" U.S. Appl. No. 11/712,028, filed Feb. 28, 2007, Office Action, mailed Dec. 27, 2007, 9 pgs.

Pereira, "Method for Predicting Sepsis or an Acute Infectious Inflammatory Response" U.S. Appl. No. 11/712,028, filed Feb. 28, 2007, Office Action, mailed Jun. 23, 2008, 7 pgs.

Pereira, "Method for Predicting Sepsis or an Acute Infectious Inflammatory Response" U.S. Appl. No. 11/712,028, filed Feb. 28, 2007, Request for Continued Examination and Amendment, mailed Nov. 10, 2008, 11 pgs.

Pereira, "Method for Predicting Sepsis or an Acute Infectious Inflammatory Response" U.S. Appl. No. 11/712,028, filed Feb. 28, 2007, Office Action, mailed Dec. 15, 2008, 11 pgs.

Pereira, "Method for Predicting Sepsis or an Acute Infectious Inflammatory Response" U.S. Appl. No. 11/712,028, filed Feb. 28, 2007, Amendment, mailed Jun. 10, 2009, 15 pgs.

Pereira, "Method for Predicting Sepsis or an Acute Infectious Inflammatory Response" U.S. Appl. No. 11/712,028, filed Feb. 28, 2007, Notice of Allowability, mailed Aug. 28, 2009, 4 pgs.

Pereira, "Method for Predicting Sepsis or an Acute Infectious Inflammatory Response" U.S. Appl. No. 11/712,028, filed Feb. 28, 2007, Response to Interview Summary, mailed Sep. 22, 2009, 2 pgs.

Pereira, "Method for Detecting a Chronic Inflammatory-Associated Disease" U.S. Appl. No. 12/697,906, filed Feb. 1, 2010, Office Action, mailed Apr. 14, 2010, 20 pgs.

Beran et al., "Heparin-binding protein as a biomarker of circulatory failure during sever infections: A report of three cases" *Scandinavian Journal of Infectious Diseases* (2010) vol. 42, pp. 634-636.

Berkestedt et al., "Elevated plasma Levels of Antimicrobial Polypeptides in Patients with Severe Sepsis" *J. Innate Immun.* (2010) vol. 2, pp. 478-482.

Changho et al., "Neutrophils in biliary atresia. A study on their morphologic distribution and expression of CAP37" *Pathology-Research and Practice* (2010) vol. 206, pp. 314-317.

Linder et al. "Heparin-binding protein: A diagnostic marker of acute bacterial meningitis" *PubMed* (Dec. 31, 2010) Abstract (1 page).

Linder et al., "Heparin-Binding Protein: An Early Marker of Circulatory Failure in Sepsis" *Major Article* (Oct. 1, 2009) vol. 49, pp. 1044-1050.

Linder et al., "Roles of Heparin-Binding Protein in Bacterial Infections" *J. Innate Immun.* (2010) pp. 1-8.

Pereira et al., "CAP37, an inflammatory mediator in Alzheimer's disease" *The FASEB Journal* (2008) vol. 22, p. 167.11, Abstract (1 page).

Olczak et al., "Structural analysis of N-glycans from human neutrophil azurocidin." Biochem. Biophys. Res. Comm. Apr. 26, 2002, No. 293, No. 1, pp. 213-219.

* cited by examiner

BIOMARKER AND METHOD FOR DETECTING A CHRONIC INFLAMMATORY-ASSOCIATED DISEASE

CROSS REFERENCE TO RELATED APPLICATIONS

This application is a continuation-in-part of U.S. Ser. No. 12/697,906, filed Feb. 1, 2010, now abandoned, which is a continuation of U.S. Ser. No. 11/712,028, filed Feb. 28, 2007, now U.S. Pat. No. 7,655,480, which is a continuation-in-part of U.S. Ser. No. 10/384,474, filed Mar. 7, 2003, now abandoned, which claims the benefit of U.S. Ser. No. 60/363,114, filed Mar. 8, 2002, each of which is hereby expressly incorporated herein by reference in its entirety.

STATEMENT REGARDING FEDERALLY SPONSORED RESEARCH OR DEVELOPMENT

This invention was made with Government support under Public Health Service Grant AI-28018-06 awarded by National Institute of Allergy and Infectious Disease. The Government has certain rights in the invention.

BACKGROUND

The present invention relates to, but is not limited to, methods for detecting chronic and acute inflammatory-associated diseases by detecting CAP37 proteins in a body fluid.

Cationic Antimicrobial Protein of $M_r$ 37 kDa (CAP37) was originally isolated from granule extracts of human polymorphonuclear leukocytes (PMN) in 1984 (1). The amino acid sequence of PMN-CAP37 revealed its relation to members of the serine protease family that have a conserved catalytic active site consisting of his-57, asp-102 and ser-195 in the charge relay system (2). Of these sites, the conserved histidine and serine of the catalytic triad have been replaced with serine and glycine residues, respectively, rendering CAP37 ineffective as a serine protease (2,3). However, CAP37 has been demonstrated to have a diverse and exciting repertoire of functions. It was first analyzed regarding its bactericidal properties against Gram negative bacteria including, but not limited to, *Salmonella typhimurium*, *Escherichia coli* and *Pseudomonas aeruginosa* (4) and its ability to bind to and neutralize lipopolysaccharide (LPS)(5). Subsequently we showed CAP37 to be a potent chemoattractant for monocytes (6). Additionally, regarding its effects on the monocyte, CAP37 has been reported to stimulate their survival and thrombospondin secretion (7), also to enhance the LPS-stimulated release of prostaglandin E2 (8), interleukin 6 (IL-6)(9) and tumor necrosis factor-alpha (TNFα)(8-10). To add even further to its extensive range of known functions, CAP37 has been demonstrated to stimulate the reversible contraction of fibroblasts and endothelial cells (7) and to activate endothelial cell protein kinase C (PKC)(11). Recently, CAP37 released from stimulated PMN was reported to be taken up and sequestered in nearby endothelial mitochondria and has been suggested to protect against apoptosis (12).

The presence of CAP37 in the endothelium of Alzheimer's brain microvessels has been shown to be induced in rat brain endothelial cells in response to stimulation with the inflammatory molecules TNFα, interleukin 1-alpha (IL-1α) and LPS (13). There is also evidence that both Alzheimer's disease (AD) and atherosclerosis are inflammatory-associated (modulated) diseases (14,15) in which inflammation and associated mediators can exacerbate or augment the disease. A simple method for the detection of the presence of or risk for chronic inflammatory-associated diseases would be desirable.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Molecular weights of the CAP37 isoforms were determined by measuring the distance migrated from the origin of the gel of each isoform and comparing this distance in mm to the distance migrated by known molecular weight markers that were electrophoresed side-by-side on a 10% SDS polyacrylamide gel. Molecular weight markers (PRECISION PLUS PROTEIN™ Kaleidoscope standards, from BioRad with a molecular weight range of 250 kDa to 10 kDa) were electrophoresed according to standard conditions along with the plasma samples. The proteins were transferred to nitrocellulose membranes for Western blots analysis. The distance migrated of each molecular weight marker and the isoforms were measured and a graph was plotted with the logarithm of the molecular weight on the X-axis and the distance migrated on the Y-axis.

Figure 12:
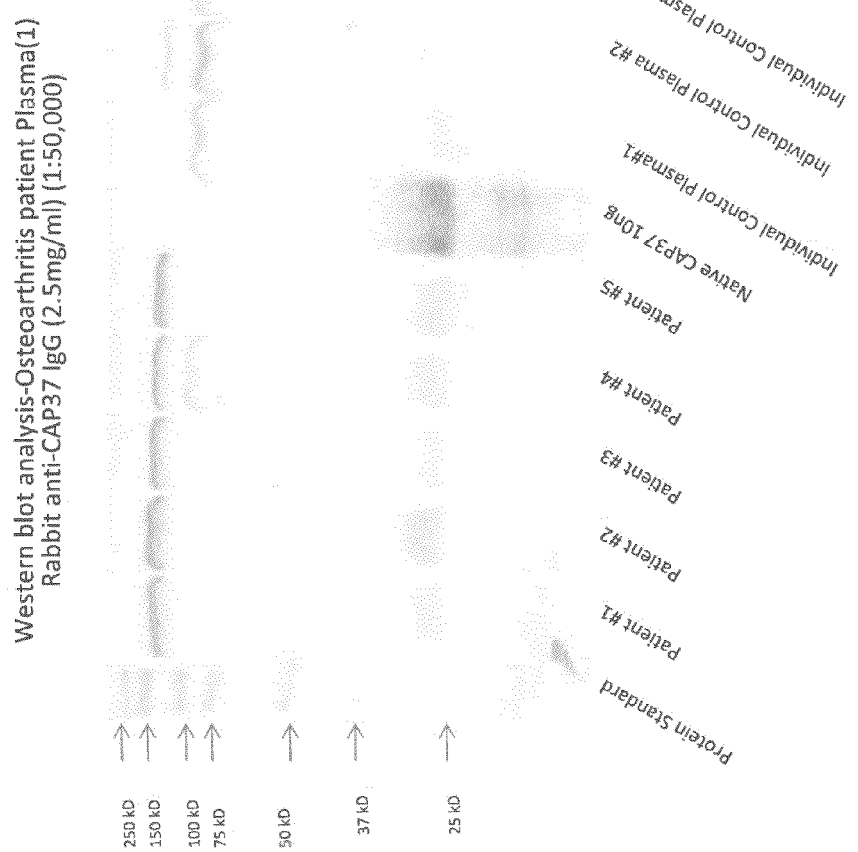
FIG. 12 is an image of a Western blot analysis of plasma samples from five patients diagnosed with osteoarthritis which shows the presence of a high molecular weight (~135 kDa) isoform of CAP37 protein in the plasma samples. The CAP37 isoform is captured by polyclonal rabbit anti-CAP37 IgG antibody (2.5 mg/ml, 1:50,000). Native CAP37 protein is shown in a band of about 28-37 kDa.
Figure 13:
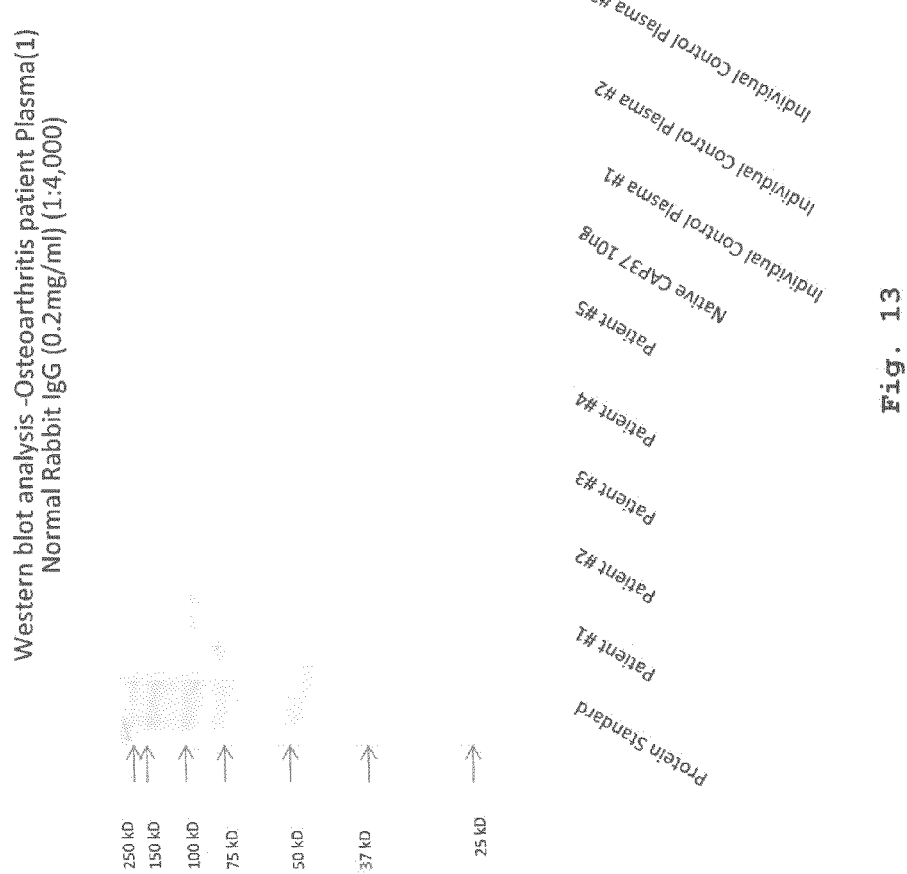

FIG. 13 is an image of a Western blot control which corresponds to the Western blot of FIG. 12 which uses normal rabbit IgG antibody.

Figure 14:
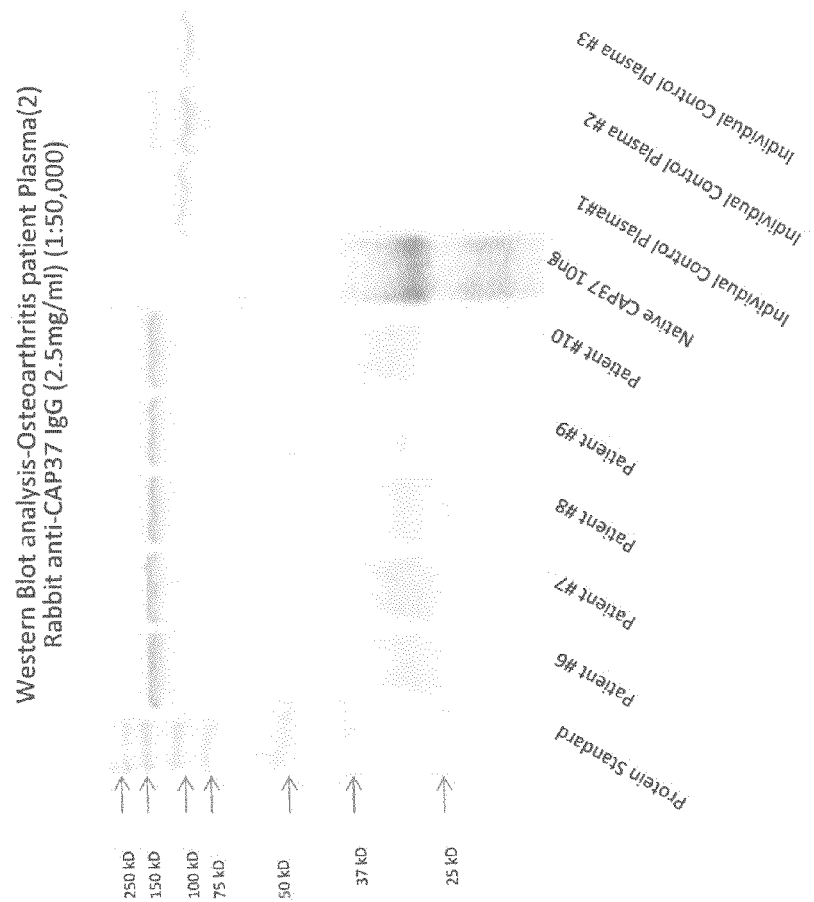

FIG. 14 is an image of a Western blot analysis of plasma samples from five additional patients diagnosed with osteoarthritis which shows the presence of a high molecular weight (~135 kDa) isoform of CAP37 protein in the plasma samples. The CAP37 isoform is captured by polyclonal rabbit anti-CAP37 IgG antibody (2.5 mg/ml, 1:50,000). Native CAP37 protein is shown in a band of about 28-37 kDa.

Figure 15:
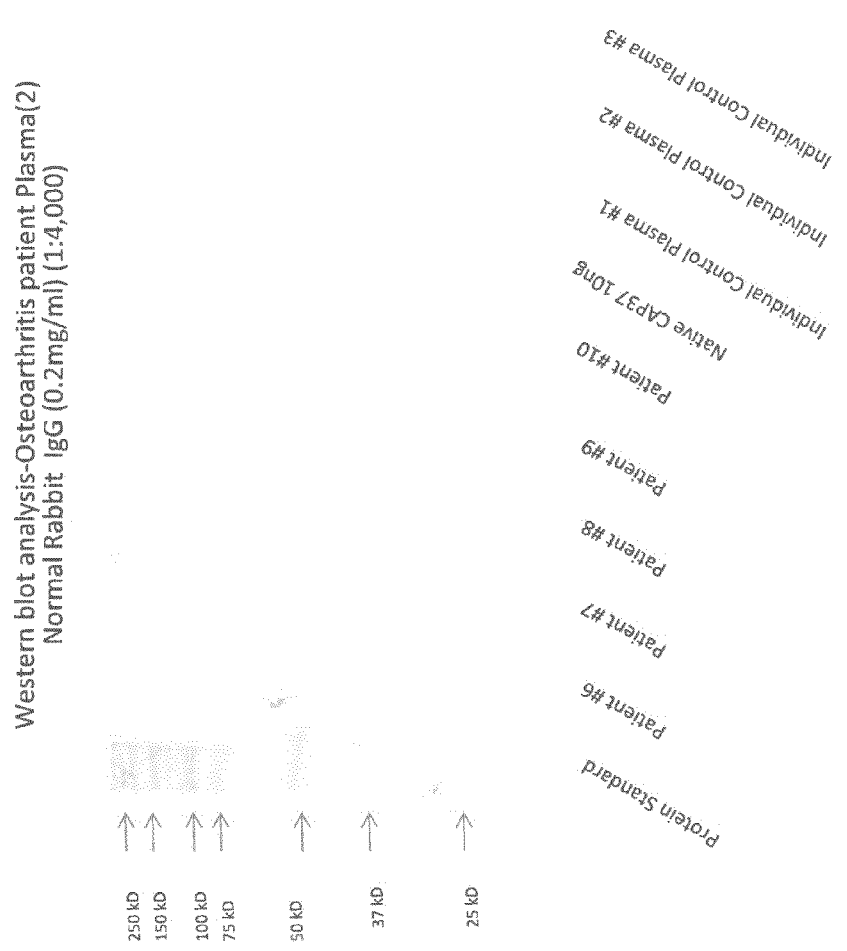

FIG. 15 is an image of a Western blot control which corresponds to the Western blot of FIG. 14 which uses normal rabbit IgG antibody.

Figure 16:
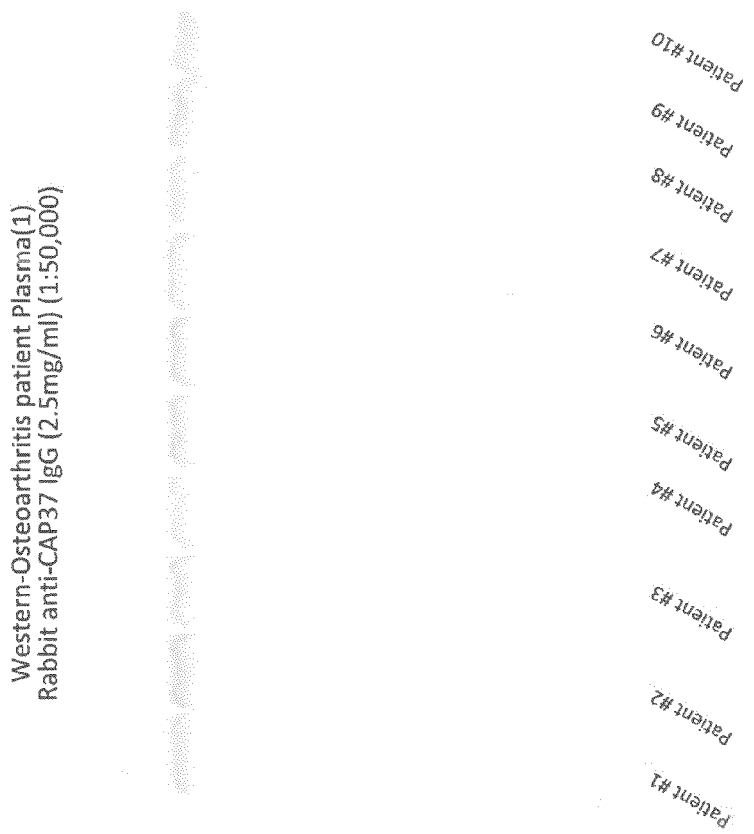

FIG. 16 is an image of a Western blot analysis showing the results for all 10 osteoarthritic patients of FIGS. 12 and 14 wherein the results showing the presence of the isoform is replicated.

Figure 17:
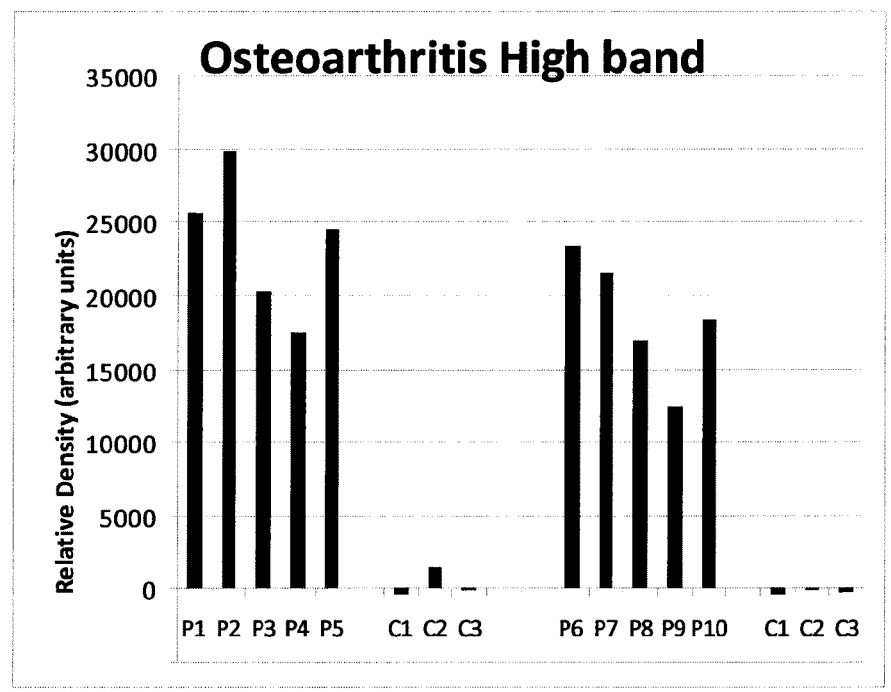
Figure 17:
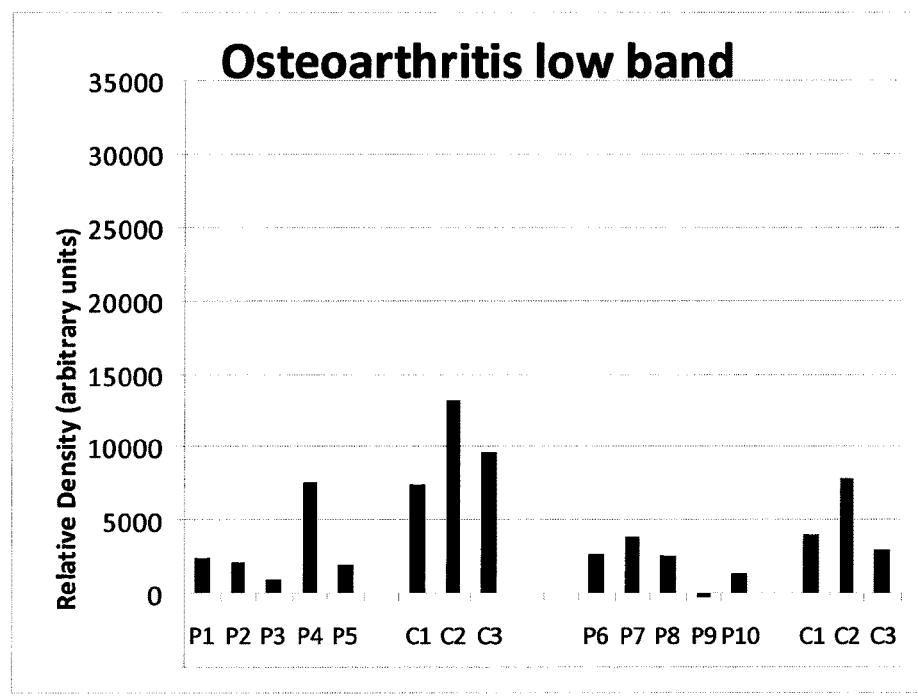

FIG. 17 are graphs showing densitometer readings in the relative units for the "high band" (~135 kDa) and "low band" (~100 kDa) results of FIGS. 12 and 14 for the 10 patients (P1-P10) and the three individual control samples (C1-C3).

Figure 18:
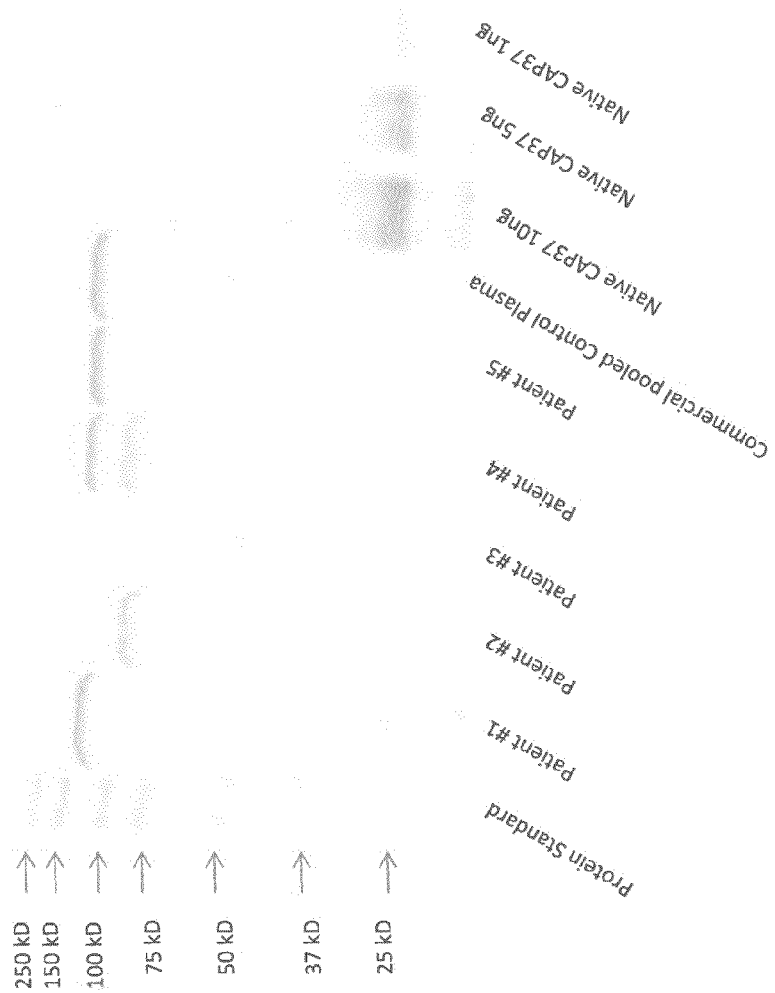

FIG. 18 is an image of a Western blot analysis of plasma samples from five patients diagnosed with atherosclerosis which show the presence therein of the high molecular weight isoform of CAP37 protein (~135 kDa) in the plasma samples of three of the five patients. The CAP37 protein isoform is captured as described above.

Figure 19:
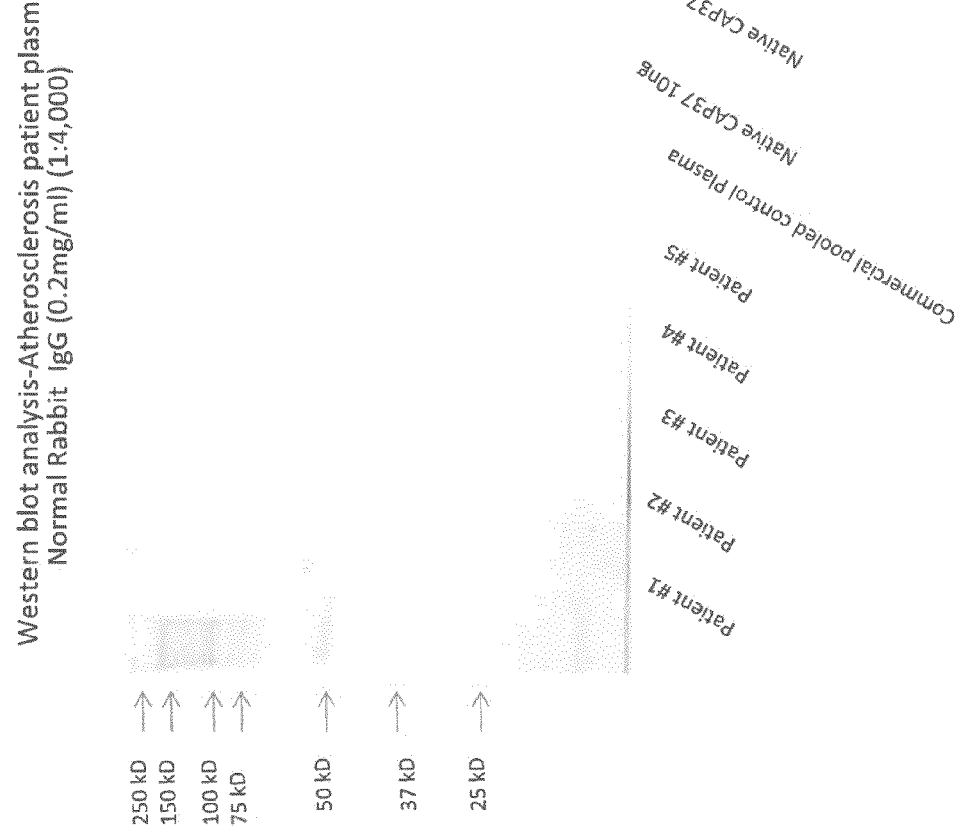

FIG. 19 is an image of a Western blot control which corresponds to the Western blot of FIG. 18 and which uses normal rabbit IgG antibody.

Figure 20:
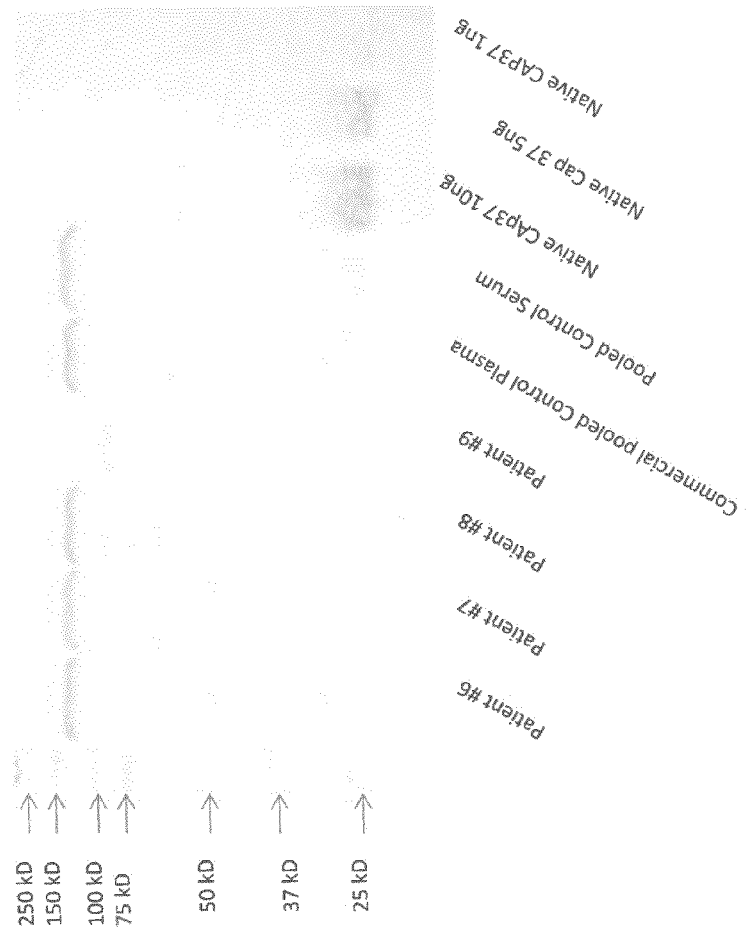

FIG. 20 is an image of a Western blot analysis of plasma samples from four additional patients diagnosed as atherosclerotic which shows the presence of the ~135 kDa CAP37 isoform in three of the four patient samples. Two "control" samples labeled as "Commercial Pooled Control Plasma" and "Pooled Control Serum" both show the presence of the ~135 kDa isoform and are suspected of being insufficiently characterized as to the source of the sample, that is, it is likely the two "control" samples may comprise plasma and serum from patients with a chronic inflammatory-related disease.

Figure 21:
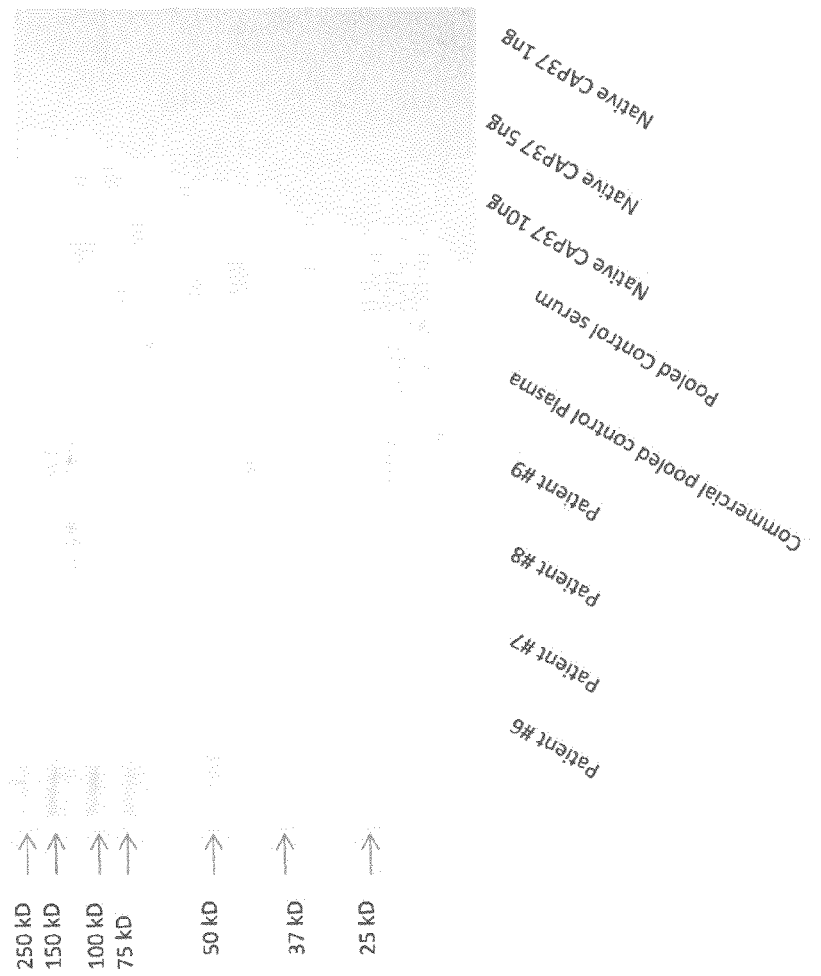

FIG. 21 is an image of a Western blot control which corresponds to the Western blot of FIG. 20 and which uses normal rabbit IgG antibody.

Figure 22:
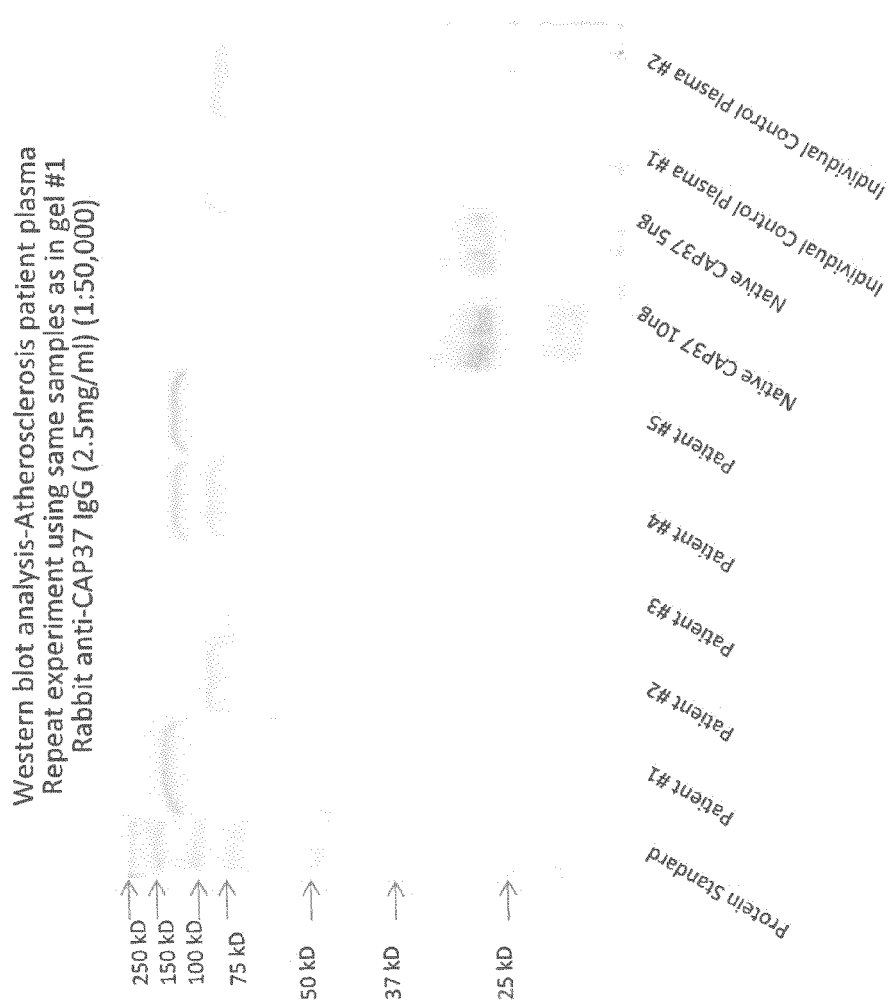

FIG. 22 is an image of a Western blot analysis which repeats the five patients from FIG. 18 against control plasma samples from two individuals. Only a faint amount of the ~135 kDa isoform of CAP37 protein appears in control sample 2 and none is apparent in control sample 1.

Figure 23:
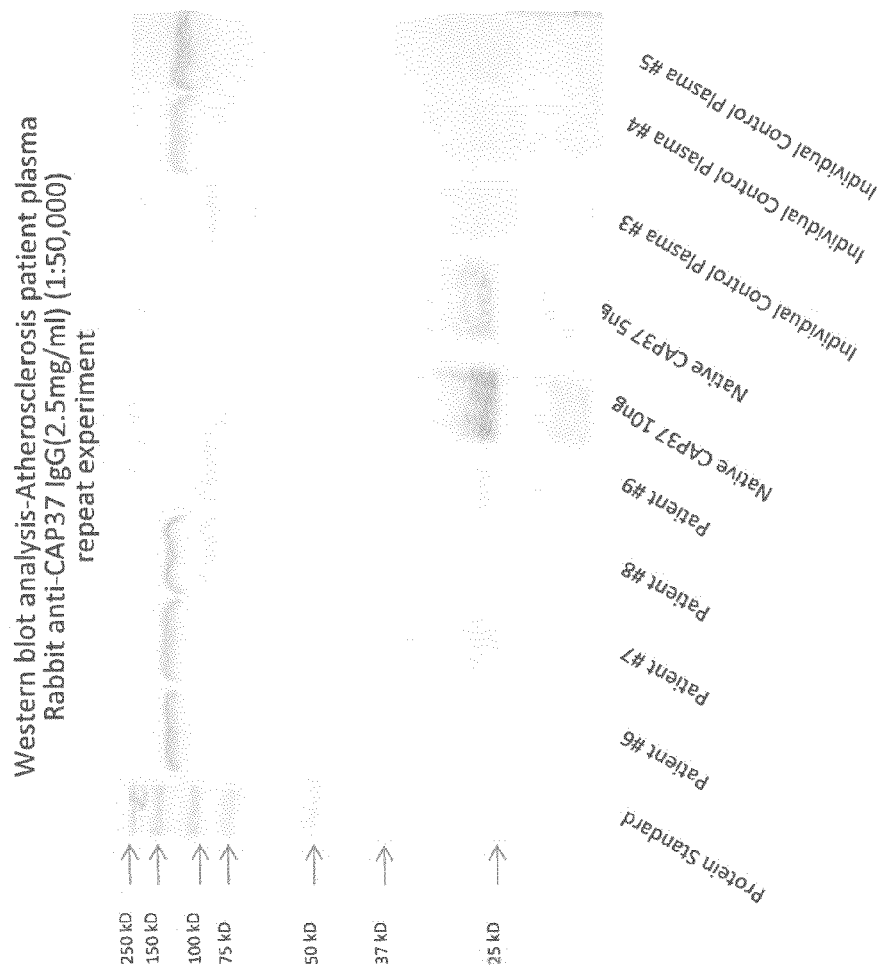

FIG. 23 is an image of a Western blot analysis which repeats the four patients of FIG. 20 against three additional control samples. Individual control sample No. 3 shows no visible amount of the ~135 kDa isoform while control samples No. 4 and No. 5 both show the presence of the ~135 kDa isoform. Again, control samples No. 4 and No. 5 were characterized only as to age (they were between 18 and 65 years of age) and not as to whether or not they had been diagnosed with a chronic inflammatory-associated disease (it is likely both suffered from a chronic inflammatory-associated disease, thus these samples are likely not true controls).

Figure 24:
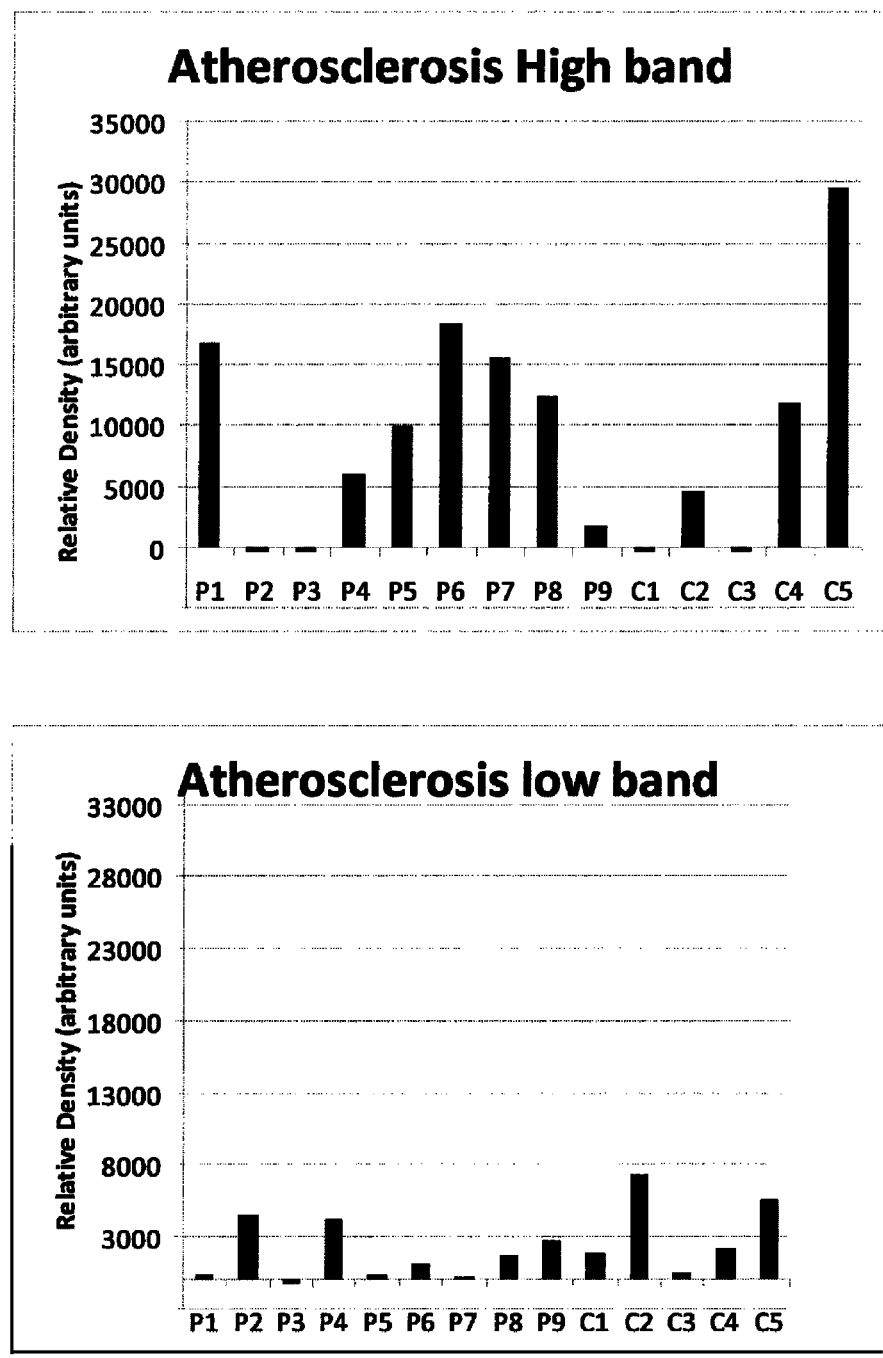

FIG. 24 are graphs showing densitometer readings in relative units for the ~135 kDa (high) and ~100 kDa (low) isoforms using the results from FIGS. 18, 20, 22 and 23.

DETAILED DESCRIPTION OF THE INVENTION

The present invention contemplates in one embodiment, a biomarker for, and a method of detecting a chronic inflammatory-associated disease in a subject. The method in one embodiment comprises (1) obtaining a fluid sample (such as serum or plasma) from the subject, preferably wherein the subject does not have an acute bacterial or viral infection when the fluid sample is obtained, (2) testing the fluid sample for a high molecular weight isoform of CAP37 protein, and (3) concluding that the subject has a chronic inflammatory-associated disease when the isoform of CAP37 protein is detected in the fluid sample. The fluid sample is preferably serum, plasma, or cerebrospinal fluid, for example, or any other body fluid exposed to endothelial, vascular, or neuronal secretions. In one embodiment the chronic inflammatory-associated disease is atherosclerosis. In another embodiment, the chronic inflammatory-associated disease is Alzheimer's disease. In another embodiment the disease is asthma. In another embodiment the disease is rheumatoid arthritis. In another embodiment the disease is osteoarthritis and/or psoriasis. In other embodiments the disease may be an inflammatory disease of the bowel, including Irritable bowel syndrome, Inflammatory bowel disease, or Crohn's disease. The isoform of CAP37 protein preferably comprises at least a portion of the protein having the amino acid sequence identified herein as SEQ ID NO: 8. In alternate embodiments, the isoforms have molecular weights of about 135 kDa (±15 kDa) or about 100 kDa (±15 kDa) as assessed by SDS PAGE under reducing conditions.

In another embodiment, the present invention comprises a method of predicting the occurrence of an acute inflammatory response in a subject (patient) due to an infection such as sepsis or other severe acute bacterial infection. In the method, a fluid sample is taken from a patient suspected of having such an infection, or susceptible to having such an infection, for example a hospitalized patient or a patient who has undergone a surgery or other procedure associated with or prone to causing systemic bacterial infections. The fluid sample is tested for CAP37 protein such as neutrophil-derived CAP37. When CAP37 protein is detected in the fluid sample, it is predicted that the patient will have sepsis or a severe acute inflammatory response due to bacterial infection. Further, the result can be used to distinguish an acute inflammatory response which is due to a bacterial infection from one due to non-infectious causes, particularly in patients for whom it is either too early to obtain accurate microbiological or bacteriological culture data or wherein treatment decisions must be made before results from such cultures can be obtained. The acute inflammatory response associated with the positive result for CAP37 protein could also be due to acute lung injury or acute respiratory distress syndrome in those individuals having severe acute pulmonary conditions. The present method may be particularly used in patients in Intensive Care Units (ICU) wherein rapid diagnosis is of critical importance.

While the invention is described below in connection with certain embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the examples described below, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

It is noted that as used herein and in the appended claims, the singular forms "a", "an", and "the" include plural reference unless the context clearly dictates otherwise. Thus, for example, reference to "an antibody" includes a plurality of such antibodies and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the presently disclosed and claimed inventive concepts, the preferred methods and materials are now described.

EXAMPLES

Example 1

Methods and Materials

Human tissues: Sections of atherosclerotic vessels (carotid, iliac, coronary and femoral arteries, and aorta) were obtained from the Department of Pathology, University of Oklahoma archival tissue bank.

Cell culture: RAECs were isolated and maintained in Dulbecco's Modified Eagle's Medium (DMEM, MEDIATECH, Herndon, Va.) supplemented with 10% fetal bovine serum (HYCLONE, Logan, Utah), as previously described (16). Cells were used within the first 15 passages.

HUVECs were isolated from umbilical cords at the University Hospital, Oklahoma City, Okla., according to methods modified from Jaffe (17). Umbilical veins were washed, flushed with PBS, and the lumen filled with 0.125% trypsin/DMEM for 15 minutes. The cell suspension was centrifuged for 5 minutes at 250×g, and the pellet resuspended in Endothelial Growth Media (EGM, CLONETICS, San Diego, Calif.) supplemented with bovine brain extract (CLONETICS). The cells were passaged at a 1 to 4 split ratio and were used in the first six passages.

Human lung microvessel endothelial cells (HMVEC-L) were purchased from CLONETICS and maintained in ENDOTHELIAL GROWTH MEDIA-2 (CLONETICS). Cells were used within passages 4-11.

Immunochemistry: Immunohistochemistry on human atherosclerotic tissue sections was performed using published methodology (13). The antiserum used was previously characterized by ELISA and shown to be specific for CAP37(13). Briefly, five μm sections were incubated at 37° C. with the primary anti-CAP37 antiserum (1:500 to 1:2000), followed by biotinylated goat anti-rabbit antiserum (VECTASTAIN ELITE), and then incubated in ABC reagent (VECTASTAIN ELITE). Color was developed with diaminobenzidine (RESEARCH GENETICS, Huntsville, Ala.) for 2-6 minutes. Sections were counterstained with hematoxylin. Antibody controls included normal rabbit serum and immunoadsorbed rabbit anti-CAP37 antiserum, as described previously (13).

For immunocytochemical analysis of rat aorta cells the media was removed and replaced with serum-free DMEM overnight prior to start of the experiment. RAEC were incubated with 10 μg/ml *S. minnesota* LPS (SIGMA, St. Louis, Mo.) for 0.5, 2, 4, 6 and 24 hours. Untreated cells at each time point were included as a control. The adherent cells on the LAB TEK slides were immunostained for CAP37 as described above (13) except the RAEC slides were fixed in ice-cold 100% methanol and the primary rabbit anti-human CAP37 antiserum was used at a 1:10 dilution.

For immunocytochemical analysis of surface expressed and cell-associated CAP37 in human endothelial cells, the media was replaced with serum free EBM (CLONETICS) 6 h prior to the start of the experiment. HUVECs were incubated in the absence or presence of 10 ng/ml TNFα for 10 and 18 h. Samples were either fixed only or fixed and permeabilized essentially as described by Grabner (18). Cells were stained as above using commercially-available normal donkey serum (5%) (JACKSON IMMUNORESEARCH LABORATORIES, INC, (West Grove, Pa.) to block nonspecific binding, rabbit anti-human CAP37 (1:750) at room temperature, biotin-sp-donkey F(ab')$_2$ anti-rabbit IgG, (JACKSON, 1:500) and peroxidase-conjugated streptavidin (JACKSON, 2 μg/ml) for amplification of signal. Staining using normal rabbit serum was included as a control.

Northern blot analysis: Total cellular RNA was isolated from RAECs (19). Thirty μg total RNA per well were run on a 1% agarose/formaldehyde gel at 80 mA for 1.5 hours. The RNA was transferred to nylon membrane overnight in SSC (3 M sodium chloride, 0.3 M sodium citrate) transfer buffer and crosslinked to the membrane with a UV crosslinker. CAP37 mRNA was detected by hybridizing a $^{32}$P-labeled CAP37 cDNA probe (6.5 μg probe at 50 μCi/blot), prepared with the PRIME-IT II RANDOM PRIMER KIT (STRATAGENE, La Jolla, Calif.), by incubating with the membrane at 60° C. overnight. Following a low (2×SSC buffer, 0.1% SDS, room temperature) and high (0.1×SSC buffer, 0.1% SDS, 60° C.) stringency wash the membrane was exposed to autoradiograph film at −80° C. To demonstrate the integrity and relative amounts of sample RNA, total cellular RNA (5 μg) was run on a 1% agarose/formaldehyde gel and visualized by ethidium bromide staining.

Western blot analysis: HUVECs were grown to confluency, serum-starved for 6 h prior to start of the experiment, and treated for 12 h with 10 ng/ml TNFα (BOEHRINGER-MANNHEIM, Indianapolis, Ind.). Cells were lysed in 1% SDS/TE (1% SDS, FISHER; TE, 1 M Tris, 0.5 M EDTA, pH 8) and 50 μg lysate were loaded per lane onto a 12.5% SDS-PAGE gel and transferred to nitrocellulose membrane (SCHLEICHER and SCHUELL, Keene, N.H.) for Western analysis (6). Briefly, blots were probed for CAP37 using a monospecific polyclonal rabbit antisera against human CAP37 (1:1000) and alkaline-phosphatase conjugated donkey anti-rabbit IgG at 1:1000 (JACKSON), and color developed with Nitro BT/5-Bromo-4-Chloro-3-Indolyl phosphate p-Toluidine salt (FISHER, Fair Lawn, N.J.). An identical blot was probed with normal rabbit serum to show specificity of the reaction. 20 μg PMN extract was included as a positive control for CAP37.

Flow Cytometry: HUVECs that were serum starved for 6 h were incubated in the absence or presence of 10 ng/ml TNFα for 10 h and 18 h. Permeabilized and non-permeabilized cells were fixed and stained essentially as described by Gräbner (18). The cells were first blocked with 4% normal donkey serum (JACKSON), then incubated at 4° C. with rabbit anti-human CAP37 antisera (1:300), and followed by biotin-sp-donkey F(ab')$_2$ anti-rabbit IgG, (JACKSON, 1:200) at 4° C. For detection the cells were incubated with fluorescein (DTAF)-conjugated streptavidin (JACKSON) at 2 μg/ml at 4° C. Cells were analyzed by flow cytometry (FACSCALIBUR, BECTON DICKINSON, San Jose, Calif.). Unstained cells and cells stained with normal rabbit serum were included as controls.

RT-PCR: HUVECs from four donors were incubated for 1 to 24 hours at 37° C. with 10 ng/ml TNFα (BOEHRINGER-MANNHEIM, Indianapolis, Ind.). The supernatant was aspirated and the cells homogenized with TRIZOL (GIBCOBRL, Gaithersburg, Md.) according to the manufacturer's instructions for total RNA isolation.

cDNA was prepared using Superscript II reverse transcriptase and oligo $dt_{12-18}$ (GIBCOBRL) essentially according to the manufacturer's protocol with an additional 30 minute incubation at 50° C. prior to termination of the reaction. cDNA was amplified in the polymerase chain reaction with primers designed for a 468 bp internal fragment (5'-GTGCTGGGTGCCTATGACCTGAGG-3' (SEQ ID NO:1) and 5'-AAGAGCGCCACTCGGGTGAAGAA-3' (SEQ ID NO:2)) flanking exons and introns of HL60-CAP37. The PCR reaction mix (1.5 mM $MgCl_2$, 0.3 mM dNTPs, 0.3 units Taq polymerase (GIBCOBRL), 0.4 μM primer mix, and cDNA in a 25 μl total volume) was amplified for 30 cycles on a BIOMETRA T GRADIENT THERMOCYCLER followed by visualization on a 1% agarose gel with 0.5 μg/ml ethidium bromide. RNA samples with no reverse transcriptase were included in the PCR reaction to demonstrate lack of genomic DNA contamination.

Cloning and sequencing of E-CAP37: RT-PCR was performed essentially as above using primers designed for an internal (5'-CAGAATCAAGGCAGGCACTTCTGC-3' (SEQ ID NO:3) and 5'-GAGAACACCATCGATC-CAGTCTCG-3' (SEQ ID NO:4)) 597 bp fragment of CAP37. The products were excised and eluted from the agarose gel with GENE CLEAN II (BIO101, Vista, Calif.) and ligated into a pCR2.1 vector (The ORIGINAL TA CLONING KIT, INVITROGEN, Carlsbad, Calif.), and cloned in INVαF' *E. coli* (ONE SHOT CHEMICALLY COMPETENT *E. coli*, INVITROGEN, Carlsbad, Calif.) according to the manufacturer's protocol. Plasmids from transformants were sequenced by the Oklahoma Medical Research Foundation Sequencing Facility in both forward and reverse directions using the T7 and M13 reverse primers for 4 clones from 3 separate induction experiments. The resulting sequences were aligned using Pôle Bio-Informatique Lyonnais, Network Protein Sequence @nalysis (20) for DNA and the consensus sequence blasted against the HL60-CAP37 cDNA sequence.

Extraction, purification and sequencing of CAP37 isoforms: CAP37 proteins from endothelial, neuronal, and other sources can be purified and sequenced, in particular for identifying C- and/or N-terminal portions which extend from the SEQ ID NO:7 portion of the CAP37 protein. For example, Rapid Amplification of cDNA ends (RACE) can be used to identify C- or N-terminal sequences of inducible isoforms of CAP37.

RACE enables the amplification of either 5' or 3' end of a specific cDNA starting from a mRNA population. The GIBCO BRL 5' and 3' RACE system can be used, for example. Total cellular RNA is isolated from stimulated endothelial and neuronal cells with TRIzol® reagent (GIBCO-BRL) and contaminating DNA removed by DNaseI treatment. For 5' RACE, neuronal and endothelial-CAP37 cDNA is synthesized using a CAP37 specific primer 5' CTG-CAGAGGCAGTGGCAGTATCGT 3' (SEQ ID NO:5) and Superscript II, an RNase H derivative of Moloney Murine Leukemia Virus Reverse Transcriptase. After the first strand cDNA synthesis, the template mRNA is removed by RNase H treatment and the remaining cDNA purified on a spin cartridge. An oligo-dC sequence is added to the 3' end of the cDNA and amplified by PCR using an Abridged Anchor Primer (GIBCO-BRL) and a second, nested CAP37 specific primer (5' GCAGAAGTGCCTGCCTTGATTCTG 3' (SEQ ID NO:6). The cDNA is re-amplified with the same nested CAP37 specific primer and either the Abridged Universal Amplification or the Universal Amplification Primer. 3' RACE is performed similarly. First strand cDNA synthesis primed with an adapter primer, followed by purification of the cDNA by digesting with RNase H. Amplification is performed using a new CAP37 specific primer (5' CGAGACTG-GATCGATGGTGTTCTC 3' (SEQ ID NO: 7), and an oligo dT specific adapter primer. The PCR product may be reamplified using the Abridged Universal Amplification Primer. 5' RACE controls include the omission of RT. Specificity of the anchor primer for the oligo-dC tail is examined by performing amplification reactions with cDNA subjected to dC-tailing both in the presence and absence of TdT. Additional controls that amplify dC-tailed cDNA using each primer individually may be required to identify non specific products that result from mispriming. The PCR products are analyzed by agarose gel electrophoresis (1.4%) and visualized with ethidium bromide staining. A single prominent band on agarose gel is produced by the procedures.

Additional rounds of PCR using successively nested CAP37 specific primers and either the Universal Amplification Primer or the Abridged Universal Amplification Primer may be required. A dilution of the original PCR is used as target. The nested primer is composed of sequences located 3' to the original CAP37 primer. For 5' RACE this is an antisense primer that anneals closer to the mRNA 5' end.

After amplification, 5' RACE products are cloned. Cloning from as little as 1 to 10 µg of the PCR product has been obtained with the CloneAmp pAMP1 system. An alternative cloning technique using the 3' to 5' exonuclease activity of the T4 DNA polymerase may also be used. The PCR products are cloned into the pCR 2.1 plasmid.

DNA sequencing: Sequencing is performed using standard methods, such as the Sequencing Core Facility (Oklahoma Medical Research Foundation) using an ABI automated sequencer which can then determine the sequence homology between CAP37 isoforms and PMN-CAP37.

An alternate method of solubilizing and extracting CAP37 isoforms is to use a combination of reverse phase and hydrophobic interaction HPLC to separate functionally active CAP37 from PMN granule extracts using 0.1 M glycine pH 3.0 to solubilize and extract the proteins. The extract is applied over a C4 reverse phase column equilibrated in solvent A (0.1% trifluoroacetic acid/2% acetonitrile/98% water). The purification is performed in a two-step gradient. A linear gradient is run to 20% solvent B in 0.4 min, followed by a second linear gradient from 20-75% in 40 min. Solvent B consists of 0.08% TFA/90% acetonitrile/10% water. The fractions are then screened by dot blot for positive reactions with anti-CAP37 antiserum. Further purifications may be performed on a Biogel TSK phenyl, 5PW hydrophobic-interaction HPLC column. In one embodiment, CAP37 can be released into the supernatant by treating the cells with increasing concentrations of heparin as has been shown for certain heparin-releasable proteins that are also heparin binding. In other cases, CAP37 solubilization can be achieved by using solutions of varying salt concentration (0.15 to 0.5 M NaCl) and pH (acidic buffers of pH 3-5, or basic buffers of pH 8-12). EDTA and EGTA may need to be added to destabilize bonds that are enhanced by $Ca^{2+}$ or $Mg^{2+}$.

Alternatively, solubilization may be performed by detergent extraction typical for an amphipathic protein, prior to purification. Crude membrane fractions are prepared by freeze thawing the cells followed by further mechanical disruption using homogenization. A cocktail of protease inhibitors (PMSF at 75 µg/ml, leupeptin at 1-10 µg/ml, pepstatin A at 1-10 µg/ml and/or a combination of 1 mM EDTA and 1 mM EGTA) is incorporated in this step. A series of non-ionic detergents can be used such as NP-40, TRITON™ X-100 OR TRITON™ X-114. Further extraction of the pellet at pH 11 for 10-30 min may be required. As for certain $Ca^{2+}$ binding proteins like the annexins, further extractions may be required using octyiglucoside or 1% zwitterionic detergents such as CHAPS. Once extraction is achieved, gel filtration followed by one or more of the described purification techniques will be used to purify the CAP37 protein.

Depending on the detergent of choice, a mixture of detergent-protein micelles, detergent-lipid protein-micelles and small membrane fragments will be obtained. Large pore resins such as SEPHACRYL® S-300 and S-400 are used since protein-detergent complexes are substantially larger than the protein alone. The eluted fractions are screened by ELISA, followed by SDS-PAGE and Western blot and those fractions reacting with the CAP37 antiserum are further isolated/purified using affinity chromatography and HPLC as described below:

Affinity chromatography using a rabbit anti-CAP37 column: Extracts are applied to rabbit anti-CAP37 affinity column or mouse anti-CAP37 column. The fractions are eluted and monitored at $A_{214}$ nm (CAP37 is not well detected at $A_{280}$ nm) for protein and then assayed by ELISA for positive fractions.

Affinity chromatography using a bovine pancreatic trypsin inhibitor (BPTI) column: CAP37 binds with high affinity to BPTI. The sample is applied to 1 ml column consisting of MINI-LEAK™ (KEN EN TEC BIOTECHNOLOGY) coupled with 30 mg BPTI. CAP37 is eluted using 0.1 M glycine pH 3.0.

Reverse-phase and hydrophobic interaction HPLC: These methods have been used previously for the purification of PMN-CAP37 (2, 3, 6, 21). Additional modifications with RP-HPLC are the use of 60% (v/v) formic acid in the application buffer and a mixture of 60% (v/v) 2-propanol and 40% (v/v) formic acid in the elution buffer. The use of either formic or acetic acid in these buffer systems improves resolution and yield of hydrophobic proteins. Fractions that react positively in dot blots from any one of the above methods are analyzed by silver-stained SDS-PAGE, and western blot to determine extent of purification.

Amino acid sequence analysis of proteins: When homogeneous protein is obtained, sequencing is performed by desalting by reverse phase HPLC and the N-terminus sequence determined using the 470A gas phase protein sequencer. The phenylthiohydantoin (PTH)-amino acids are determined on-line with the PTH analyzer. If protein preparations are not sufficiently homogeneous, the sequence of the N-termini can be determined with sufficient separation of the proteins on SDS-PAGE. Samples are run on SDS-PAGE, transferred onto IMMOBILON P membrane and stained with Coomassie Blue. The relevant bands are cut out of the membrane, and directly subjected to sequencing. If the amino terminus is blocked, the proteins are subjected to in-gel and/or in-membrane tryptic digestion. The peptides produced are separated by purification on a UMA micro HPLC system, a technique used to obtain sequence information on N-terminally blocked proteins.

Production of monoclonal antibodies (MAbs) against CAP37: MAbs were produced by immunizing 3 female, 6-8 weeks old, BALB/c mice (NCI, Bethesda, Md.) with 20 μg of cleaved recombinant CAP37 (rCAP37) emulsified in RIBI (Corixa, Hamilton, Mont.) according to the vendor's instructions, in a total volume of 100 μl, intraperitoneally (i.p.). Cleaved rCAP37 was obtained by treating rCAP37 with Factor Xa (Pierce) at an enzyme to susbstrate ratio of 1:10 to remove the HPC4 epitope. The mice were immunized 3 times as above, with a 4 week interval between each immunization. Four weeks after the final i.p. injection of cleaved rCAP37 in RIBI, the mice received 20 μg cleaved rCAP37 intravenously in 200 μl of saline solution. The mice were euthanized three days later and the spleens removed for fusion.

Hybridomas were produced by fusing spleen cells from the immunized BALB/c mice with the mouse plasmocytoma cell line SP2-0 in 50% polyethylene glycol (Sigma, St. Louis, Mo.). Hybridomas were selected with hypoxanthine-aminopterine-thymidine (HAT) medium (Sigma) and positive clones producing IgG against CAP37 were detected by ELISA using cleaved rCAP37 and neutrophil lysate as antigens. Stable reactive hybridomas were selected and cloned at least three times by limiting dilution. The MAbs were then purified, from tissue culture supernatants using a Protein-G Sepharose 4 Fast Flow column (Amersham Pharmacia Biotech, Piscataway, N.J.) following the manufacturer's protocol. The purity of MAbs was observed by gel electrophoresis stained with CodeGel Blue Stain Reagent (PIERCE). A total of 9 culture supernatants demonstrated antibodies against CAP37. From these, two hybridoma cell lines were stabilized and continuously monitored and were found to continue to secrete anti-CAP37 antibodies after 3 sub clonings by limiting dilution. These monoclonal antibodies were designated as D5F10 and B1B5. Both antibodies recognized the native and recombinant forms of CAP37.

To determine the specificity of the monoclonal antibodies for CAP37 we used ELISA and Western blot analysis according to our standard protocols. The antibodies were tested for cross reaction against other neutrophil-derived proteins including myeloperoxidase, lactoferrin, defensins, cathepsin G, and elastase. Both techniques indicated that the monoclonal antibodies D5F10 and B1B5 only recognized the rCAP37 and native CAP37 protein, with no cross reaction with the other proteins.

The monoclonal antibodies were isotyped using an ELISA isotyping kit (PIERCE). Monoclonal antibody D5F10 was an IgG1 antibody and monoclonal antibody B1B5 was an IgG3 antibody. Both of them contained k light chains.

In addition to demonstrating the specific reaction with recombinant CAP37 and native CAP37 we were able to identify the different epitopes or domains of the CAP37 molecule that were recognized by the two monoclonal antibodies. Peptides based on the native CAP37 sequence were synthesized so as to span the full length of the molecule. The peptides were designated as 1-25, 20-44, 38-53, 50-77, 70-97, 95-122, 120-146, 140-165, 160-185, 180-202, and 197-222, and named according to the number of the amino acid of the native CAP37 molecule. Dot blot analysis with D5F10 and B1B5 was performed according to standard protocols. Monoclonal antibody D5F10 recognized an epitope between amino acids 20-44, a region known to be involved with the bactericidal property of CAP37, plus additional epitopes located between amino acids 180-202 and 197-222. Monoclonal antibody B1B5 recognized an epitope between amino acids 95 and 122, a region involved in the chemotactic effect of CAP37, plus an epitope in the C-terminal region corresponding to amino acids 197-222. Immunohistochemical staining showed that monoclonal antibodies D5F10 and B1B5 reacted with the granule contents of human peripheral blood neutrophils, which is the location of constitutively expressed neutrophil-CAP37. The monoclonal antibodies did not stain other peripheral blood leukocytes which included eosinophils, monocytes and lymphocytes. A control mouse isotype antibody did not stain human neutrophils, indicating the specificity of the two monoclonal antibodies for CAP37.

Monoclonal antibody, D5F10 which recognized the CAP37 epitope between amino acids 20-44 inhibited bactericidal activity of the recombinant CAP37 and native CAP37. Monoclonal antibody B1B5 which reacted with peptide 95-122, inhibited the chemotactic activity of native and recombinant CAP37 for human monocytes and human corneal epithelial cells.

Results

The results in summary indicate that (1) CAP37 is present in atherosclerotic plaques, (2) CAP37 can be induced in cultured endothelial cells, (3) a predominant portion of endothelial derived CAP37 (referred to herein as E-CAP37) is identical to PMN-CAP37, and (4) E-CAP37 is mainly cell-associated.

Figure 1:
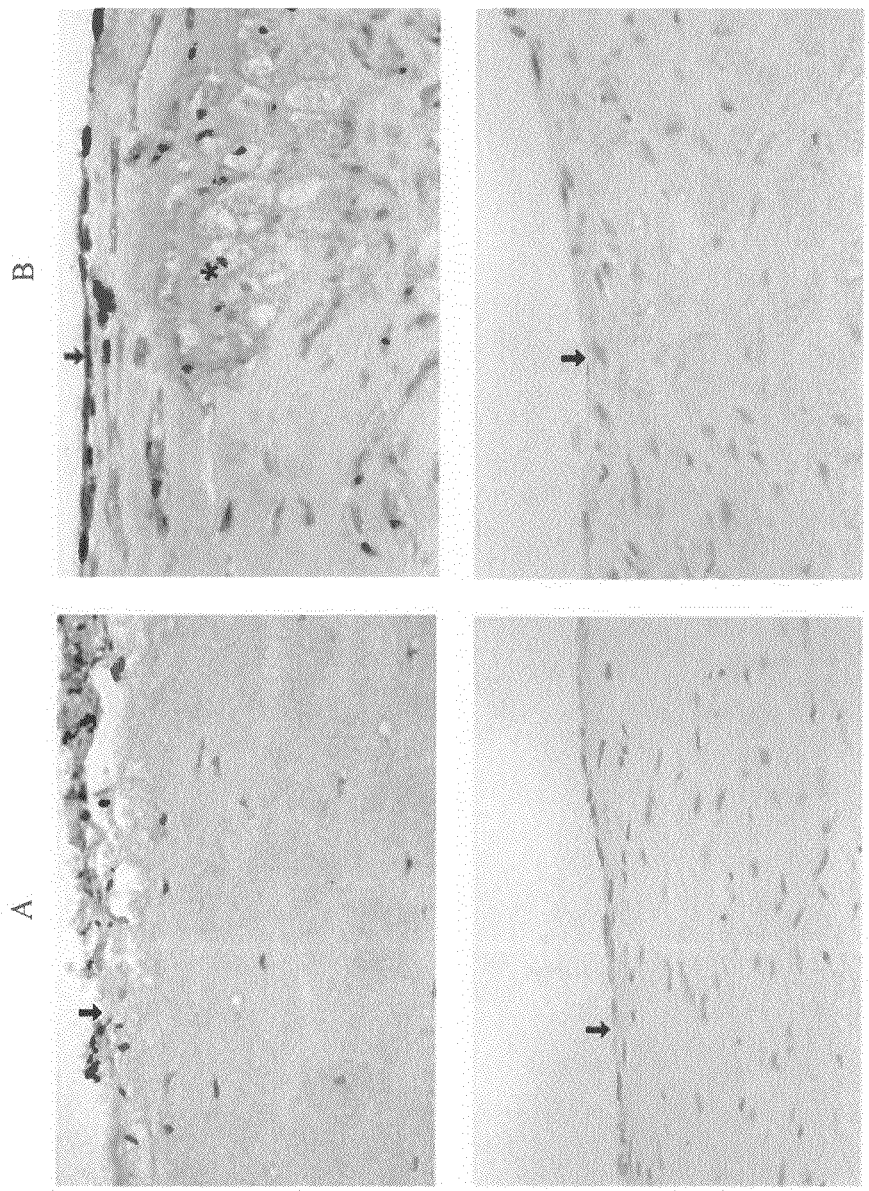
FIG. 1: Localization of CAP37 in formalin-fixed, paraffin embedded carotid artery. A: Immunohistochemistry performed on atherosclerotic lesion present in the carotid artery using antisera to human CAP37 and the VECTASTAIN ELITE technique as described elsewhere herein. Strong staining indicated the presence of CAP37 in the endothelium (×400). B: Detection of CAP37 in advanced atherosclerotic plaque indicating strong positive staining in endothelium and foam cells (×400). C: Normal vessel stained with antisera to CAP37 indicating an absence of CAP37 in "normal" endothelium (×400). D: Atherosclerotic lesion stained using an immunoadsorbed antisera to CAP37 which shows no staining (×400). The lack of staining in D indicates the specificity of the antisera for CAP37 used in these assays. Sections were counterstained with hematoxylin. ↓ indicates endothelium; * indicates foam cell.

Tissue sections from human atherosclerotic lesions showed strong staining for CAP37 in the endothelium associated with the plaque area (FIG. 1A). CAP37 was also detected in and around foam cells and cholesterol clefts in plaques with advanced disease (FIG. 1B). Normal endothelium away from the injured endothelium associated with the plaque did not stain for CAP37 (FIG. 1C). Antibody controls using immunoadsorbed antisera to CAP37 (13) showed no staining for CAP37 (FIG. 1D) indicating the specificity of the reaction obtained in FIGS. 1A, 1B and 1C.

Since CAP37 was detected in the endothelium of atherosclerotic plaques but not in normal endothelium, it was hypothesized that CAP37 was induced in response to injurious and/or inflammatory mediators. To explore this possibility we obtained endothelial cells from various vascular beds including rat aorta (RAECs), human umbilical vein (HUVECs), and human lung microvessel (HMVEC-L) and treated these cell cultures with LPS and cytokines including TNFα and IL-1. We used immunocytochemical, Northern blot analysis and RT-PCR to detect CAP37. The immunocytochemical data presented here (FIG. 2) were obtained from RAECs. CAP37 protein was detected in LPS-treated endothelial cells as early as 2 h. Maximum staining was obtained between 4 h (FIG. 2A) and 6 hours. Staining was reduced, but still evident at 24 hours. Untreated cells (FIG. 2B) did not stain at any of the time points with anti CAP37 antiserum. Antibody controls using normal rabbit serum showed virtually no background staining. Similar studies using HUVECs and HMVEC-Ls indicated expression of CAP37 in response to LPS (data not shown).

Figure 3:
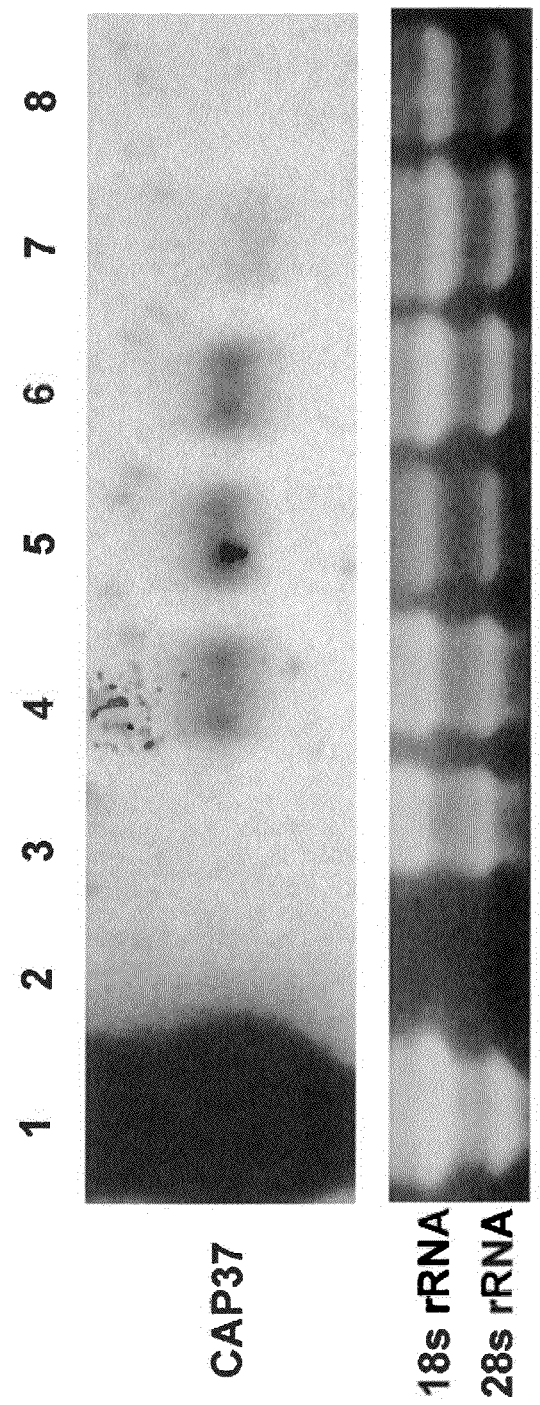
FIG. 3: Northern blot analysis of CAP37 mRNA in RAEC. Rat aorta endothelial cells were stimulated for 0 (Lane 3), 0.5 (Lane 4), 2 (Lane 5), 4 (Lane 6), 6 (Lane 7) and 24 hours (Lane 8) with *Salmonella minnesota* LPS and the Northern blot performed on total RNA from each time point using the $^{32}$P-labeled CAP37 cDNA probe as described in text. An HL-60 cell line (Lane 1) used as a positive control indicated presence of CAP37 mRNA (1000 bp). 18S and 28S rRNA (lower panel) of total cellular RNA demonstrating the integrity and relative amounts of RNA. Lane 2 is empty.

To further corroborate our immunocytochemical data we isolated total cellular RNA from unstimulated RAECs and RAECs stimulated with 10 μg/ml S. minnesota LPS over a time course spanning 30 minutes to 24 hours and performed Northern blot analysis to identify CAP37 mRNA. Using a $^{32}$P-labeled CAP37 cDNA probe, we detected CAP37 mRNA at 30 minutes in LPS-stimulated cultures. CAP37 mRNA was also present in 2, 4 and 6 hour stimulated cultures but was not detected at 24 hour (FIG. 3). We did not detect CAP37 mRNA in unstimulated cultures at any time point. An HL-60 cell line (abundant in CAP37 mRNA)(21) was used as a positive control.

Figure 4:
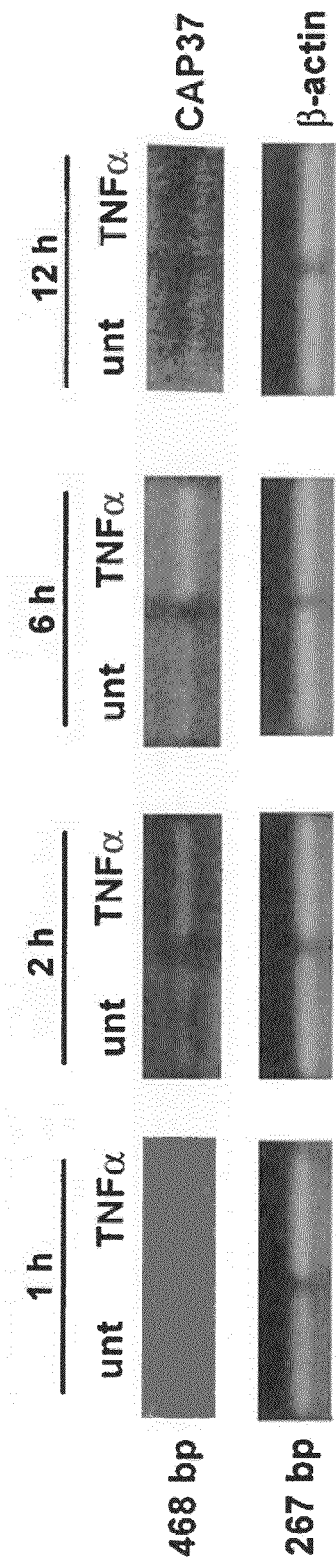
FIG. 4: RT-PCR analysis of human umbilical vein endothelial cells (HUVECs) for CAP37 mRNA. Human umbilical vein endothelial cells were incubated with 10 ng/ml TNFα (TNFα) or left untreated (unt) for the indicated times and CAP37 mRNA expression (upper panel, 468 bp) determined by RT-PCR. cDNA integrity was assessed with β-actin primers (lower panel, 267 bp). This is a representative figure of five independent experiments.

In addition to the above studies with LPS-treated RAECs we demonstrated the induction of CAP37 in HUVECs in response to the inflammatory cytokine TNFα. We performed these studies by incubating HUVECs in the absence or presence of 10 ng/ml TNFα. CAP37 mRNA induction was assessed by RT-PCR. Kinetic studies performed over a 24 hour time period indicated that CAP37 mRNA significantly increased following TNFα stimulation. Initial upregulated expression was observed as early as 1 hr and in general persisted for a 6 hr time period (FIG. 4). In certain experiments, upregulated expression of CAP37 was observed as late as 12 h. In contrast to the northern blot data using RAECs, we observed constitutive CAP37 mRNA expression in HUVECs using RT-PCR. RT-PCR was performed with primers designed to flank exons and introns of CAP37 so that any genomic DNA contamination would be readily apparent (appearing as a PCR product much larger than that obtained from cDNA). In addition, the control PCR reactions using RNA samples containing no reverse transcriptase did not detect genomic DNA contamination.

Final confirmation that we were in fact dealing with CAP37 was obtained from sequence data. We cloned an extensive region of E-CAP37 and compared the cDNA sequence to the known HL60-CAP37 (21) sequence. This comparison demonstrated complete identity with amino acids 19-217 (SEQ ID NO:8) of PMN-CAP37.

To determine whether the induced form of CAP37 was cell associated or released, a series of experiments was undertaken that included immunocytochemistry, flow cytometry, ELISA and western blot analysis. In the immunocytochemical studies, we treated HUVECs with TNFα and compared the staining pattern for CAP37 in fixed cells with permeabilized cells. FIG. 5A indicates that there is virtually no CAP37 detected when cells are fixed but not permeabilized indicating that there is very minimal, if any, cell surface expressed CAP37. This is true regardless of whether cells are treated with TNFα (FIG. 5A) or remain untreated (FIG. 5B). On the other hand, when TNFα treated cells are permeabilized we observe dramatic staining for CAP37 indicating that a major component of endothelial CAP37 is cell associated (FIG. 5C). The staining is punctuate throughout the cytoplasm with visible perinuclear localization. Untreated cells indicate a minimal amount of intracellular staining (FIG. 5D) in comparison to the treated cells. Antibody controls using normal rabbit serum show absence of staining in TNFα treated cells (FIG. 5E).

Figure 5:
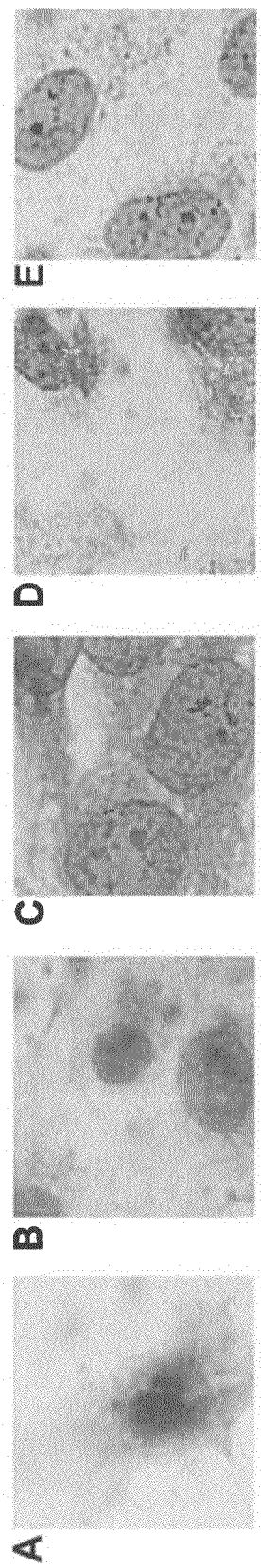
FIG. 5: Immunocytochemical assessment of surface bound and cell-associated CAP37 in HUVECs. A: HUVECs incubated with TNFα for 10 h, fixed (but not permeabilized), and stained with antisera to CAP37 indicating no staining for CAP37 on the outer surface of the cell (×1000). B: Untreated HUVECs, fixed but not permeabilized and stained with antisera to CAP37 indicating lack of staining (×1000). C: HUVECs incubated with 10 ng/ml TNFα for 10 h, permeabilized and stained with antisera to CAP37 indicating strong cytoplasmic and perinuclear staining for CAP37 (×1000). D: HUVECs incubated with media alone for 10 h, permeabilized, and stained with antisera to CAP37 indicating light intracellular staining (×1000). E: HUVECs incubated with media alone for 10 h, permeabilized, and stained with normal rabbit serum indicating no staining (×1000).
Figure 6:
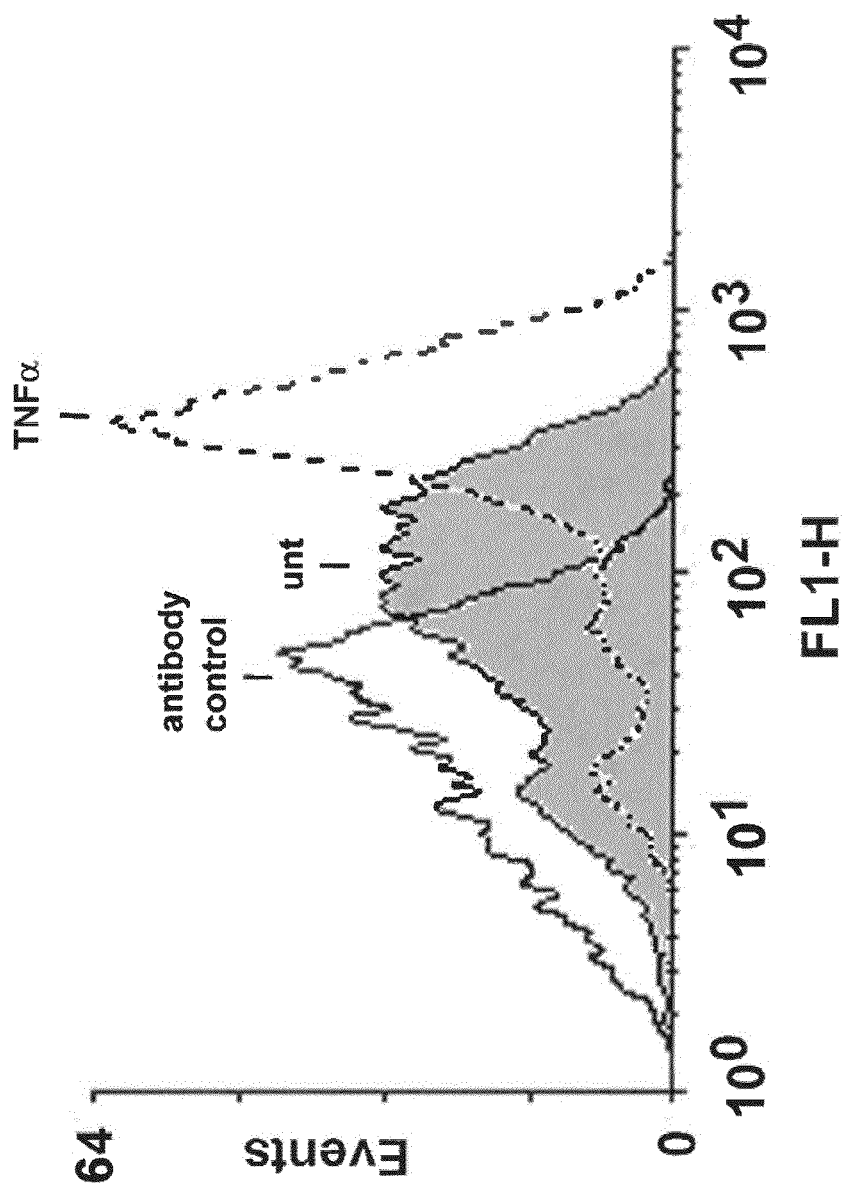
FIG. 6: Flow cytometric analysis of cell associated CAP37 in HUVECs. HUVECs were incubated 18 h in the absence (unt) or presence of 10 ng/ml TNFα (TNFα), permeabilized and labeled with antisera to human CAP37 or normal serum control. Cells were permeabilized to determine intracellular levels of CAP37. A representative histogram from two independent experiments. The shift due to FITC-staining indicates increased expression of CAP37 in TNFα stimulated cells. Also indicated is a low level of constitutive CAP37 expression (unt).

Flow cytometry confirmed the studies described in FIG. 5. TNFα treated cells that were permeabilized indicated up to a 5-fold increase of CAP37 expression over untreated cells (FIG. 6). Once again, the data indicated that there is a low level of constitutive expression of CAP37 protein in HUVECs. No detectable surface expression of CAP37 was observed in non-permeabilized cells using flow cytometry irrespective of whether cells were treated or untreated (data not shown). To determine whether CAP37 is released from treated endothelial cells, we used ELISA to analyze supernatants from TNFα treated HUVEC cultures. Levels of released CAP37 from treated HUVECs were two-fold over untreated cells (data not shown). It was clear that the amount and proportion of CAP37 released from HUVECs was in general much less than the amount and proportion of CAP37 released from PMN (6). Almost 90% of total CAP37 is released from PMN following phagocytosis (6).

Figure 7:
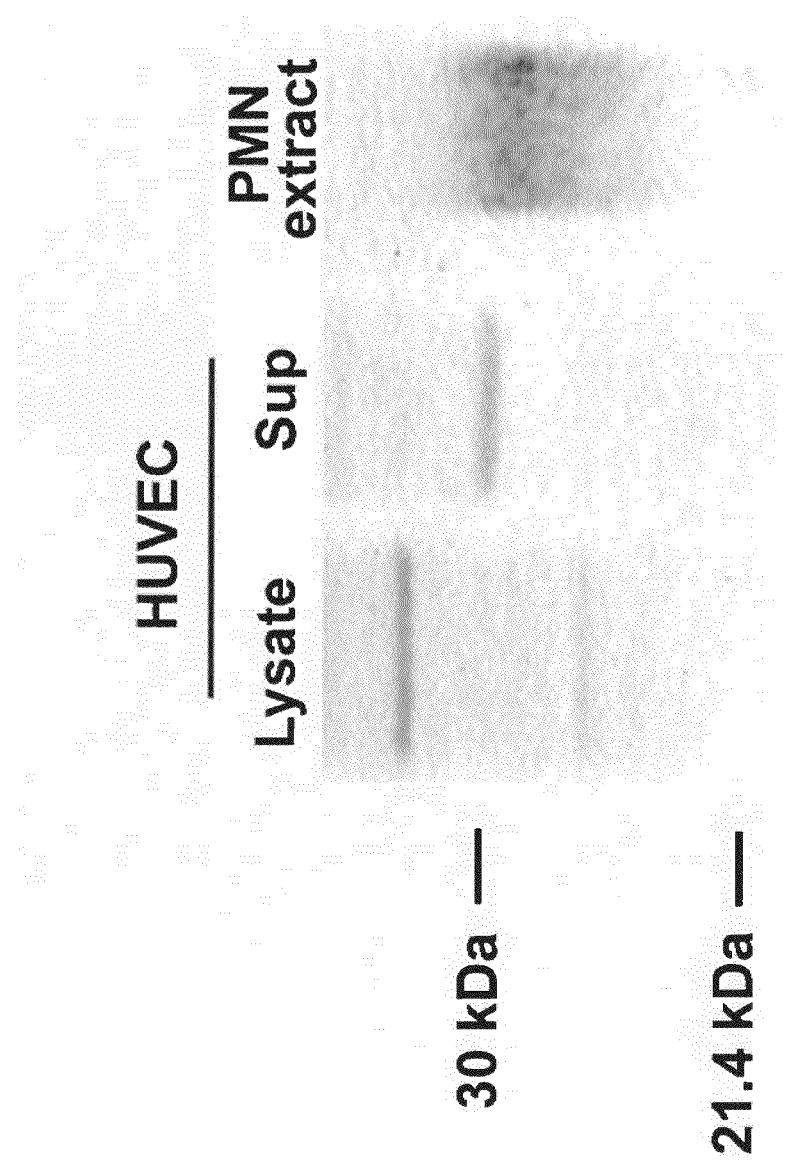
FIG. 7: Western blot analysis of HUVECs for CAP37 protein. Human umbilical vein endothelial cells were incubated with TNFα. 50 µg total protein was loaded into each lane. CAP37 protein expression, both cell associated (lysate) and released (sup), was determined using rabbit antisera to human CAP37. PMN extract (20 µg) included as a positive control for CAP37 staining.

Western blot analysis of HUVEC lysates and supernatants from TNFα treated cells was performed to provide information regarding the molecular mass and processing of the various CAP37 species. FIG. 7 indicates an extremely interesting finding. The released form of CAP37 from HUVECs appears to have a molecular mass closely correlating with the major form of PMN-derived protein, and is clearly a single species. However, there are two forms of the cell associated form of endothelial CAP37, one that migrates with a molecular mass of approximately 26 kDa and another stronger band at approximately 33 kDa. Due to the differential glycosylation of PMN-derived CAP37, the protein migrates as a smear on SDS-PAGE with a range of molecular mass between 24 to 37 kDa. Normal rabbit serum, used as a control antibody to probe an identical blot showed no reaction with HUVEC lysate, supernatant, or PMN extract indicating the specificity of the antiserum used (data not shown).

Example 2

In addition to the expression of CAP37 in atherosclerosis, we have further demonstrated its expression in an inflammatory mediated disease of the central nervous system, viz Alzheimer's disease (AD).

CAP37 is expressed in hippocampal neurons exhibiting granulovacuolar degeneration (FIG. 8A). Fine granular deposits throughout the neuropil also stained positive for CAP37. AD Brains from individuals with Alzheimer's disease which were stained with normal mouse serum (FIG. 8B) showed no staining in neurons, indicating the specificity of the staining for CAP37. Normal age-matched control brains from non-demented persons showed extremely weak to no staining for CAP37 in neurons (FIG. 8C) microvasculature, and neuropil. Antibody controls using normal mouse serum showed no staining (FIG. 8D). Immunohistochemical staining performed on sections form patients with other neuropathologic conditions showed no staining for CAP37 in neurons.

Figure 9:
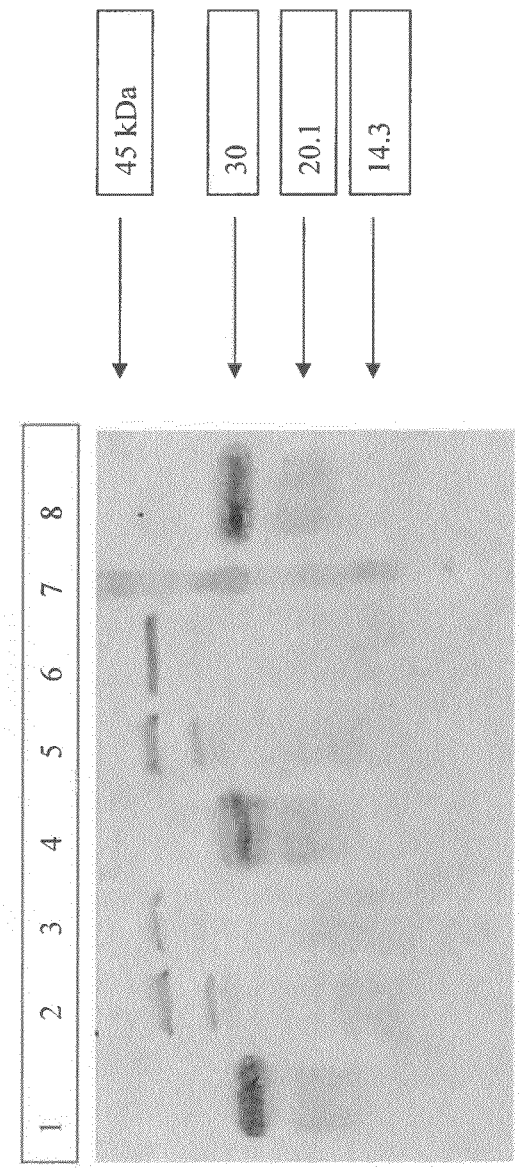
FIG. 9: Western blot analysis of extracts of AD brains and normal age-matched controls with anti-CAP37 antiserum. Lane 1, PMN CAP37; lane 2, AD patient #1; lane 3, control #1; lane 4, PMN CAP37; lane 5 AD patient #2; lane 6, control #2; lane 7, m.w. markers; lane 8, PMN CAP37. Equivalent amounts of protein (4.6 µg) loaded in AD and control lanes and 300 ng of purified CAP 37.

Western blot analysis on extracts of brain tissue from two different Alzheimer's disease patients and two age-matched controls (FIG. 9) indicated the reaction of two molecular species in Alzheimer's disease patients with the anti-CAP37 antiserum. One band migrated at approximately 46 kDa and the other at approximately 40 kDa. The larger band was present in age-matched controls as well; however, the 40 kDa band was specific to Alzheimer's disease patients. The 40 kDa band is a neuronal CAP37 having a slightly greater molecular weight than PMN CAP37.

Figure 10:
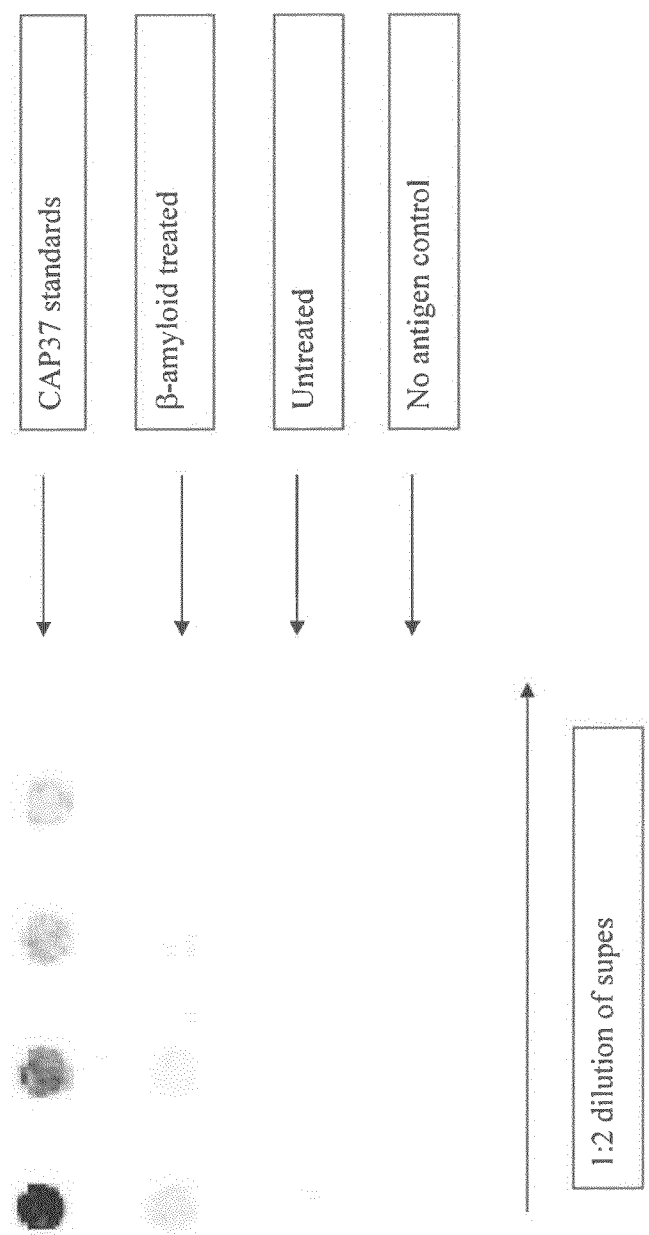
FIG. 10: Dot blot analysis of supernatants from human neuronal cells in vitro with anti-CAP37 antiserum. Top row (from left to right) consists of CAP37 standards, at 20, 10, 5 and 2.5 µg/ml. $2^{nd}$ row consists of doubling dilutions of supes from β-amyloid treated neuronal cultures. Row 3 consists of doubling dilutions of supes from untreated neuronal cultures. Row 4—no antigen/control.
Figure 11:
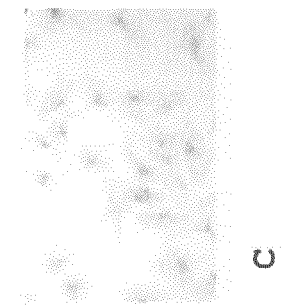
FIG. 11: Immunocytochemical localization of CAP37 in cultured human neurons. A. HCN-1A neurons were cultured and treated with β-amyloid (75 pg/ml) and stained with anti-CAP37 antiserum. Strong staining was obtained within cells after 12 hr of treatment. B. Neurons treated with β-amyloid and reacted with normal mouse serum show no staining for CAP37. C. Untreated cells with anti-CAP37 antiserum also show no staining indicating that CAP37 is not constitutively expressed in neurons but is induced (×400).
Figure 11:
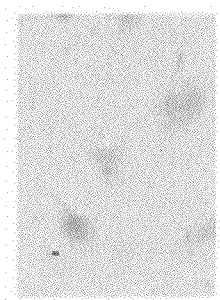
Figure 11:
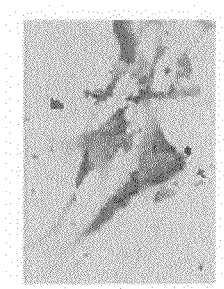

The expression of CAP37 in neurons was further corroborated using in vitro culture. Human neuronal cells (ATCC, HCN-1A) were cultured according to specifications, transferred to serum-free medium for 6 hr and treated with β-amyloid fragment 1-42 (75 µg/ml), control peptide 40-1 (75 µg/ml), and media for 12 hrs. Supernatants were analyzed by dot blot for presence of released CAP37 (FIG. 10) and cells stained with anti-CAP37 antiserum (FIG. 11A) and normal mouse serum (FIG. 11B) to determine cell-associated CAP37. As can be seen CAP37 is not present in untreated neurons (FIG. 11C), but is strongly expressed in cells treated with β-amyloid, and can be detected as a released (secreted) form in supernatants at a concentration of approximately 2.5 µg/ml.

The association of CAP37 with diseases such as Alzheimer's disease, osteoarthritis, and atherosclerosis, as shown herein, indicates that CAP37 is an important mediator of inflammation leading to the exacerbation or augmentation of chronic inflammatory responses observed in inflammatory-associated (mediated) diseases such as Alzheimer's disease, osteoarthritis, atherosclerosis, psoriasis, and others described herein.

The present invention, as contemplated herein, therefore comprises in one embodiment a diagnostic test for atherosclerosis, osteoarthritis, psoriasis, Alzheimer's disease, and other chronic inflammatory-associated (mediated) diseases including asthma, rheumatoid arthritis, and inflammatory diseases of the bowel such as Crohn's disease, Ulcerative colitis, Irritable bowel syndrome and Inflammatory bowel disease.

Figure 8:
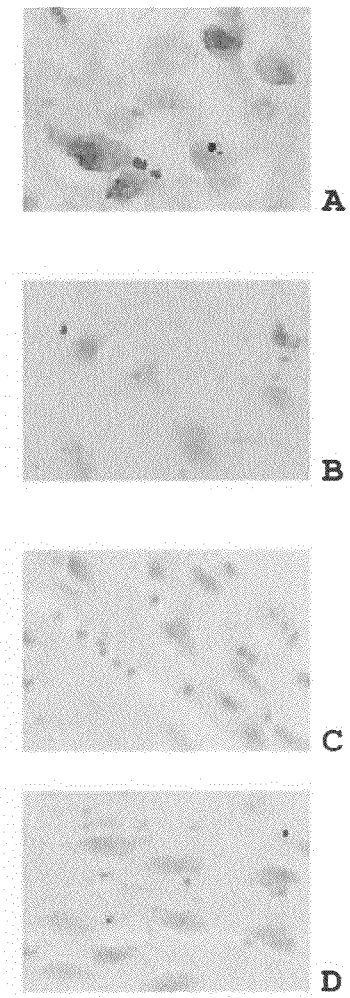
FIG. 8: Immunocytochemical localization of CAP37 in AD (A & B) and normal control brain (C & D). Sections were stained using monospecific mouse anti-human CAP37 antiserum (1:1000) and normal mouse serum (1:1000) and the VECTASTAIN-ABC-PEROXIDASE technique. A. AD brain with anti-CAP37 serum showing strong positive stain in neurons (×400). B. AD brain with normal mouse serum showing negative stain in neurons (×200). C. Normal age-matched control brain with mouse anti-CAP37 antiserum showing lack of staining in neurons (×200). D. Normal age-matched control with normal mouse serum (×200).

The results shown herein demonstrate novel and important observations about the inflammatory mediator CAP37. Firstly, we have convincingly demonstrated its presence in atherosclerotic lesions and in and round foam cells, and cholesterol clefts in complex plaques. Secondly, we have demonstrated its presence in vascular endothelium and neurons of Alzheimer's disease patients (FIG. 8). Thirdly, we have demonstrated the presence of induced forms of CAP37 in endothelial cells and neuronal cells in response to cytokines and injurious mediators such as LPS and TNFα which are related to inflammatory diseases. This is the first demonstration of endogenous endothelial or vascular CAP37 and of a secreted neuronal CAP37.

Sequence analysis demonstrated substantial homology between E-CAP37 and PMN-CAP37, with a complete match of 199 amino acids from residue 19 through residue 217 (SEQ ID NO:8, which is encoded by the cDNA SEQ ID NO:9). This homologous region includes coding sequence for the domains of PMN-CAP37 reported to have bactericidal (22) and endotoxin neutralizing (5) activity. The region reported to activate PKC (11) in endothelial cells is also included within this region. Mature PMN-CAP37 is a 222 amino acid molecule (including SEQ ID NO:8) and having a calculated molecular mass of approximately 24 kDa (3). Molecular masses ranging from 37 kDa to 24 kDa have been observed on SDS-PAGE due to its differential glycosylation (3). Based on the calculated molecular mass of one form of endothelial CAP37 observed on our Western blots one would expect to find differences/extensions at the amino- and/or carboxy terminus end of the molecule. It is not unusual for inducible and constitutively expressed forms of the same molecule to have variations in size and amino acid sequence. This has been well documented for IL-12 (23,24).

In addition to the differences in molecular mass between inducible E-CAP37 and PMN-derived CAP37, our results suggest differences relating to the processing of E-CAP37. Previous findings from our laboratory indicate that PMN-derived CAP37 is easily released from the granules of the PMN on activation, with almost 90% of total CAP37 detected in supernatant fluids (6). On the other hand, E-CAP37 comprises distinct cell-associated and released forms. The cell-associated protein migrated as a higher kDa band while the released protein migrated equivalently to the PMN-derived protein. The two isoforms of IL-1, for example, also demonstrate a differential pattern of extracellular release, IL-1β is easily released, whereas IL-1α is not (25).

Figure 2:
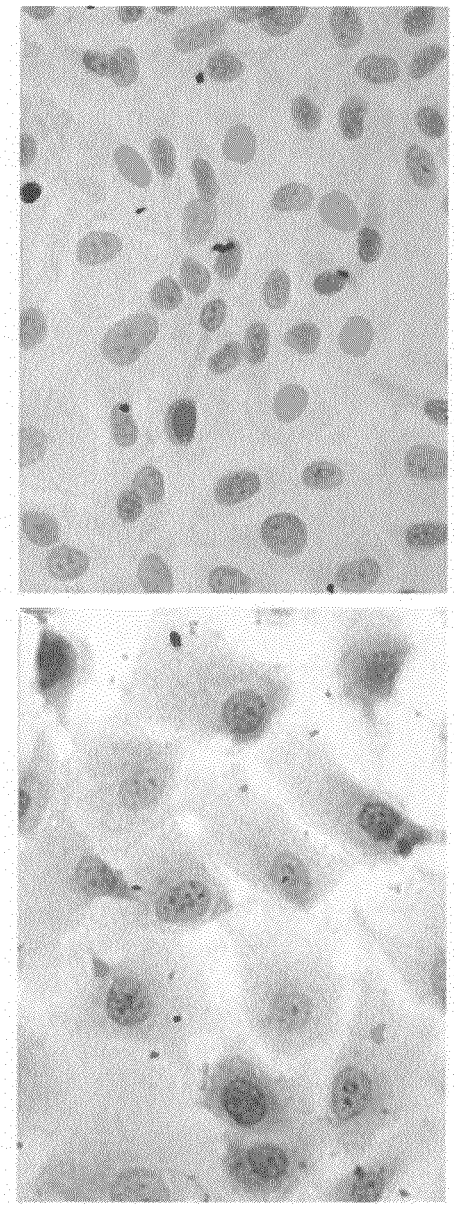
FIG. 2: Induction of CAP37 protein in rat aorta endothelial cells (RAECs). A: Immunocytochemistry of RAECs stimulated with 10 μg/ml LPS for 4 hours and stained with antisera to CAP37 using the VECTASTAIN ELITE ABC technique indicating strong staining for CAP37 (×400). B: RAECs incubated with media alone and stained with antisera to CAP37 shows no positive reaction, indicating that E-CAP37 is not constitutively expressed in RAECs (×200). Sections were counterstained with hematoxylin.

To explore the identity of the mediators involved in the induction of CAP37 in endothelium we undertook a series of in vitro studies. In FIG. 2, we demonstrated immunohistochemically, that CAP37 is induced in endothelial cells in response to the injurious mediator, LPS. Kinetic studies showed that CAP37 protein was induced in rat aorta endothelial cells in vitro by LPS as early as 30 minutes, peaked at 4-6 hours, and subsided by 24 hours. Corroborative studies using Northern blot analysis demonstrated the expression of CAP37 mRNA to follow a similar time course in which expression is no longer detected at 24 hours of LPS stimulation. The antiserum used for these experiments was raised against human CAP37 (13), and the probes used for the northern blot analysis were based on the human CAP37 sequence (21) indicating that there is significant conservation of CAP37 across species (6,11,27). The present studies were performed using rat aorta endothelial cells since we believed that endothelial cells derived from the aorta would be the most appropriate site for studies dealing with atherosclerosis. It is important to note that this induction of CAP37 in endothelial cells does not appear to be limited to the aorta. Other studies from our laboratory indicate that TNF-α and IL-1α can induce CAP37 in cultured endothelial cells from rat cerebral microvessel endothelial cells (13) and as described in FIGS. 4 through 7 can also be induced in HUVECs and in HMVEC-Ls. It's particularly interesting that PMN-CAP37 is entirely constitutive and cannot be induced. In fact, mature PMN lack mRNA for CAP37 (21). In endothelial cells the constitutive expression of basal mRNA and protein levels appeared to vary. As seen in the figures with rat aorta we found no constitutive levels even at the mRNA or protein level whereas our study with HUVECs and HMVEC-Ls indicated some constitutive expression. This may reflect the species from which the cells are obtained, since rat cerebral vessel showed no constitutive expression either (13).

Our immunohistochemical data on atherosclerotic lesions demonstrate that the expression of CAP37 protein is not confined solely to the endothelium but is also detected throughout the cholesterol clefts, foam cells, and proliferating smooth muscle cells in the subintimal area of advanced lesions. Our data further indicate that the CAP37 expressed in the endothelium is endogenous E-CAP37. The CAP37 in the smooth muscle cells is of endogenous origin, since ongoing studies in our laboratory indicate that CAP37 is expressed in proliferating smooth muscle cells. Following injury to the endothelium, platelets and/or PMN will adhere to it due to upregulation of various adhesion molecules, and on activation will release CAP37. In addition, CAP37 is induced in endothelial cells in response to inflammatory cytokines. The presence of exogenous and endogenous CAP37 sets up a chemotactic gradient across the endothelium which ensures recruitment and migration of monocytes. CAP37 could also contribute to endothelial contraction (7) further influencing the transmigration of leukocytes across the endothelium.

As shown herein, a neuronal form of CAP37 has been identified in the neurons of patients dying from Alzheimer's disease. In vitro tissue culture assays performed in our laboratory using human neuronal cell lines show that CAP37 in induced in human neurons in response to the toxic 42-amino acid beta-amyloid peptide. This was assayed by immunohistochemistry using mouse anti-CAP37 antiserum and by dot blot assay. The dot blot assay was performed on supernatants collected from the cell cultures and indicates that the CAP37 is liberated into the supernatants without any physical or mechanical perturbation of the cells. Thus it is evident that neuronal CAP37 of subjects suffering from Alzheimer's disease is easily released into the extracellular milieu wherein the neuronal CAP37 can be identified and assayed in either in the cerebrospinal fluid or in the patient's plasma or serum.

Example 3

Osteoarthritis

Plasma samples from 10 patients who were diagnosed with osteoarthritis (and who did not have an active acute infection) were analyzed using SDS-PAGE under reducing conditions followed by Western blot analysis (using the techniques described previously). The only difference in the Western blot procedure of Examples 3 and 4 versus that used in Examples 1 or 2 was that the purified IgG fraction of the rabbit antibody to CAP37 was used, and was used at a much higher dilution (1:50,000) in the Western blots (wherein the prior blots used the primary antibody at 1:1,000). These samples were obtained from BioServe Biotechnologies Ltd, Beltsville, Md. These patients were also diagnosed with psoriasis, another chronic inflammatory-associated disease. "Control" plasma samples were taken from 3 individuals who were asked if they had an active acute infection (and answered negatively) but they were not explicitly asked if they had been diagnosed with osteoarthritis. Gels were loaded with patient samples and control samples and following electrophoresis were transferred to nitrocellulose for western blot analysis. The blots were probed with polyclonal rabbit anti-CAP37 IgG (2.5 mg/ml-1:50,000) (FIGS. 12, 14 and 16). The control western blots (FIGS. 13 and 15) were probed with normal rabbit IgG (0.2 mg/ml-1:4,000). The lack of reactivity in the control blots showed that the rabbit anti-CAP37 antibody was specific for CAP37. The results revealed strong bands corresponding to an apparent molecular weight (MW) of about 135 kDa (±15 kDa) in all ten osteoarthritis patients (FIGS. 12, 14 and 16). These bands constitute isoforms of CAP37 protein which are distinguished from polymorphonuclear (neutrophil-derived) CAP37 ("native CAP37" on the gels) which has a MW of 29-37 kDa, depending on its glycosylation level.

Control samples from individuals (C1, C2 and C3) in FIGS. 12 and 14, show a lower band comprising a CAP37 isoform having an apparent molecular weight of about 100 kDa (±15 kDa). One patient sample (P4) comprised this ~100 kDa isoform, and one individual control sample (P2) comprised the ~135 kDa isoform (indicating that this control individual may have some level of osteoarthritis or other chronic inflammatory-associated disease such as atherosclerosis).

The data are summarized in FIG. 17 where it is shown that amounts of the ~135 kDa isoform ("High Band") in the patient samples (P1-P10) are substantially greater than any amounts of this isoform found in the control samples (C1-C3).

Normal rabbit IgG used for the Western blots came from Jackson ImmunoResearch Laboratories, Inc., WestGrove, Pa. The product is referred to in their catalog as ChromPure Rabbit IgG, whole molecule. The secondary antibody used in the Western blots also cam from Jackson ImmunoResearch Laboratories, Inc. The product is referred to as Alkaline Phosphatase-conjugated affiniPure Donkey anti-rabbit IgG (heavy and light chain). The primary antibody rabbit anti-CAP37 IgG was prepared in-house according to standard procedures.

Example 4

Atherosclerosis

Plasma samples from 9 patients who were diagnosed with atherosclerosis (and who did not have an active acute infection) were analyzed using SDS-PAGE under reducing conditions followed by Western blot analysis (using the techniques described previously for Example 3). These samples were obtained from Asterand, plc Detroit, Mich. Gels were loaded with the patient samples and the control samples and following electrophoresis were transferred to nitrocellulose for western blot analysis. The blots were probed with polyclonal rabbit anti-CAP37 IgG (2.5 mg/ml-1:50,000) (FIGS. 18, 20, 22 and 23). The control blots (FIGS. 19 and 21) were probed with normal rabbit IgG (0.2 mg/ml-1:4,000). The lack of reactivity in the control blots showed that the rabbit anti-CAP37 antibody was specific for CAP37. The results revealed strong bands corresponding to an apparent molecular weight (MW) of about 135 kDa (±15 kDa) in 6 of the 9 atherosclerosis patients (FIGS. 18, 20, 22 and 23). These bands, as for Example 3 above, constitute isoforms of CAP37 protein which are distinguished from polymorphonuclear (neutrophil-derived) CAP37 ("native CAP37" on the gels) which has a MW of 29-37 kDa, depending on its glycosylation level.

Samples from patients P2, P3 and P9 did not show bands of the ~135 kDa CAP37 isoform (FIGS. 18 and 20). It is suspected that these patients, who had previously been diagnosed with atherosclerosis had diminished levels of the ~135 kDa isoform due to treatment with an anti-inflammatory/immunosuppressive medication regime.

Two pooled control samples obtained from commercial sources in FIGS. 18 and 20 show an upper band comprising a CAP37 isoform having an apparent molecular weight of about 135 kDa (±15 kDa). These pooled samples were apparently not characterized as to whether or not they had a chronic inflammatory-associated disease. Thus at least one of the samples used in each pooled sample apparently had some level of a chronic inflammatory-associated disease such as atherosclerosis. These pooled control samples are thus suspect.

Five control samples (C1-C5) from individuals were analyzed (FIGS. 22 and 23). A slight amount of the ~135 kDa isoform was seen in the results for control sample C2 (FIG. 22). Dense bands for the isoform were present in the control samples C4 and C5. However, the disease history associated with these two controls was unknown. According to the research protocol of the study, no medical history could be asked, except for whether they had an active bacterial or viral infection. Samples were de-identified immediately and no identifiers were kept that could relate back to the sample according to the consenting protocol passed by the Institutional Review Board. It is likely that these two subjects had an undiagnosed or non-symptomatic chronic inflammatory-associated disease. These two control samples were thus suspect.

These data are summarized in FIG. 24 which show that the level of the ~135 kDa CAP37 isoform is substantially greater in the majority of the patient population studied as compared to a control population which comprised individual samples.

These data demonstrate that the isoform of CAP37 protein having a MW of ~135 kDa is consistently present in patients who suffer from a chronic inflammatory-associated disease such as osteoarthritis or atherosclerosis. In one embodiment, a subject is considered to have a chronic inflammatory-associated disease such as osteoarthritis or atherosclerosis if a plasma or serum sample therefrom comprises the ~135 kDa isoform of CAP37 protein, or has at least twice (2X) the amount calculated as an average of said isoform found in a control population.

Utility

The present invention contemplates in one embodiment, a method of detecting, in a subject, a chronic inflammatory-associated disease. The method comprises (1) obtaining a fluid sample from the subject, (preferably the subject does not have an acute bacterial or viral infection when the fluid sample is obtained), (2) testing the fluid sample for an isoform of CAP37 protein (a biomarker) for example by using CAP37-isoform-specific monoclonal and/or polyclonal antibodies in an ELISA or Western blot test, and (3) concluding that the subject has a chronic inflammatory-associated disease when an isoform of CAP37 protein having an apparent molecular weight of about 135 kDa is detected in the fluid sample. The fluid sample may comprise serum, plasma, or cerebrospinal fluid, for example, or any other body fluid exposed to endothelial, vascular, or neuronal secretions. In one embodiment the chronic inflammatory-associated disease is atherosclerosis. In another embodiment, the chronic inflammatory-associated disease is Alzheimer's disease. In other embodiments the disease may be asthma, rheumatoid arthritis, osteoarthritis, and inflammatory diseases of the bowel such as Crohn's disease, Ulcerative colitis, Irritable bowel syndrome and Inflammatory bowel disease. The CAP37 isoform may be endothelial CAP37, vascular CAP37, neuronal CAP37, or neutrophil-derived, for example. The isoform of CAP37 protein preferably comprises at least a portion of the protein having the amino acid sequence identified herein as SEQ ID NO: 8.

The use of CAP37 as an early marker for detection of inflammatory associated diseases would be used in concert with medical symptom associated with a given disease. For example, CAP37 as an early marker of atherosclerosis would be determined in patients at risk for heart disease having one or more risk factors including smoking, obesity, family history, chest pain and/or diabetes. CAP37 as an early marker of Alzheimer's disease would be determined in patients at risk for this disease which would include the elderly, changes in cognitions, and in persons with a family history of Alzheimer's disease. CAP37 as an early marker for asthma would be indicated in adults and children with associated symptoms of wheezing, shortness of breath and allergic reactions, for example. CAP37 as an early marker of osteoarthritis and or rheumatoid arthritis would be best determined in patients presenting swollen joints, pain in joints or stiffness in joints, for example. CAP37 as a marker of inflammatory diseases of the bowel would be best determined in patients with changes in bowel habits, extended periods of discomfort, acid reflux, bloating, and cramping and other symptoms typical of persons with inflammatory diseases of the bowel.

Plasma for use in the diagnostic test can be obtained, for example, by collecting peripheral venous blood (approximately 5 ml) from a subject by venipuncture into a sterile tube containing EDTA or sodium citrate. EDTA and sodium citrate serve as anticoagulants and stop the blood from clotting. The anti-coagulated blood may be centrifuged at the regulation speed of 1500 r.p.m. for 10 min. This permits the cellular components of the blood to settle to the bottom of the tube. The plasma can be aspirated from the top of the tube and used immediately in the assay or can be stored indefinitely in sterile tubes at −20° C. for later analysis.

Serum can be obtained, for example, by collecting peripheral venous blood (e.g., approximately 4 ml) by venipuncture into a sterile tube without any anticoagulant. The tube may be stored at room temperature until the blood clots. The tube can be centrifuged at 1500 r.p.m. for 10-15 min. The straw colored liquid on top of the clot is the serum. The serum is aspirated and can be used immediately in the assay or can be stored indefinitely at −20° C. for future analysis. Any trained phlebotomist, technician, nurse, or physician can perform the venipuncture, for example.

Cerebrospinal fluid can be collected by standard practice generally known as a spinal tap by an authorized health practitioner. The spinal fluid (for example, approximately 2-4 ml) can be used immediately in the assay or may be aliquoted and stored at −20° C. for later analysis.

The neuronal CAP37, endothelial CAP37, vascular CAP37, and neutrophil-derived CAP37 can be detected from the fluid sample using CAP37-specific monoclonal or polyclonal antibodies, such as described elsewhere herein, in a standard ELISA method well known to those of ordinary skill in the art, for example, as described in Pereira et al., 1989 (30) which is expressly incorporated herein by reference in its entirety, or the neuronal CAP37, endothelial CAP37, or vascular CAP37 may be detected by any other suitable method known in the art, for example PCR, as described elsewhere herein. Rabbit antisera and mouse antisera which are specific for CAP37 can be prepared using standard methods well known to those of ordinary skill in the art, for example, as in Pereira et al., 1996a (11) and Pereira et al., 1996b (13) which are expressly incorporated herein by reference in their entirety.

In another embodiment, the present invention comprises a method of predicting the occurrence of an acute inflammatory response in a subject (patient) due to an infection such as sepsis or other severe acute bacterial infection. In the method, a fluid sample is taken from a patient suspected of having such an infection, or susceptible to having such an infection, for example a hospitalized patient or a patient who has undergone a surgery or other procedure associated with or prone to causing systemic bacterial infections. The fluid sample is tested for CAP37 protein such as neutrophil-derived CAP37. When CAP37 protein is detected in the fluid sample, it is predicted that the patient will have sepsis or a severe acute inflammatory response due to bacterial infection. Further, the result can be used to distinguish an acute inflammatory response which is due to a bacterial infection from one due to non-infectious causes, particularly in patients in which it is either too early to obtain accurate microbiological or bacteriological culture data or wherein treatment decisions must be made before results from such cultures can be obtained. The acute inflammatory response associated with the positive result for CAP37 protein could also be due to acute lung injury or acute respiratory distress syndrome in those individuals having severe acute pulmonary conditions. The present method may be particularly used in patients in Intensive Care Units (ICU) wherein rapid diagnosis is of critical importance. Further, the test may be used in tandem with detection or measurement of another inflammatory marker, such as, but not limited to, C-reactive protein, IL-1, IL-6, or tumor necrosis factor alpha, to improve the predictability of the method.

As discussed above, on a preferred embodiment, the present invention comprises isoforms of CAP37 protein (i.e., the ~135 kDa and ~100 kDa isoforms) which may be used as biomarkers or to generate monoclonal antibodies against the CAP37 isoform protein described herein using methods well known in the art, which may be used in assays used in the detection method as described herein. Such antibodies against the isoforms of CAP37 protein are also considered to be embodiments of the invention as claimed herein. The isoforms may also be used in screening methods for identifying inhibitors of these proteins. The present invention further comprises nucleic acids, e.g., cDNAs which encode the endothelial CAP37 protein isoforms, vascular CAP37 protein isoforms, neutrophil-derived CAP37 isoforms, and neuronal CAP37 protein isoforms. The invention further comprises those amino acid portions of the endothelial CAP37, vascular CAP37, neuronal CAP37, or neutrophil-derived CAP37 proteins which do not comprise SEQ ID NO:8, i.e., the N-terminal or C-terminal potions extending N-terminally and/or C-terminally from SEQ ID NO:8.

Examples of diagnostic kits and tests for identifying the endothelial CAP37 protein isoforms in fluid samples include, but are not limited to, the examples described below.

1) Western Blot Test to Determine the Presence of the CAP37 Isoform in Plasma, Serum, or other Body Fluid.

A mono-specific rabbit antibody to the CAP37 isoform or a mouse monoclonal antibody to the CAP37 isoform is produced according to standard protocols. To produce the monoclonal and/or polyclonal antibody, the band corresponding to the CAP37 isoform can be cut out of the gel, homogenized and used as the "antigen" to immunize rabbits or mice. The standard protocol for generating polyclonal monospecific antiserum in rabbits is utilized or the standard protocols for generating monoclonal antibodies in mice are utilized. The preparation of polyclonal or monoclonal antibodies is conventional and well known to persons of ordinary skill in the art. Alternatively, the protein can be purified according to standard Reverse phase HPLC protocols to separate the CAP37 isoform from the plasma of patients. The purified protein can be used to generate the antibodies in rabbits or mice. The test comprises providing the purified CAP37 isoforms at a known concentration and the corresponding purified antibody that reacts specifically with the CAP37 isoform and of performing standard SDS-PAGE gel electrophoresis of the patient samples and the known CAP37 isoform control protein. Samples are transferred to nitrocellulose or PVDF membranes and western blot performed using the primary antibody to the CAP37 provided with the kit. Various options from commercial vendors are available for use as secondary antibodies. These include antibodies that could be used with chemiluminescence or the blots can be developed using secondary antibodies conjugated to alkaline phosphatase or other standard enzymatic reactions. Reaction with the antibody at a band corresponding in molecular weight to the known control indicates the presence of the corresponding CAP37 isoform in the patient sample.

2) ELISA to Determine the Presence of CAP37 Isoform in Plasma, Serum or other Body Fluid.

Monoclonal antibody and polyclonal rabbit antisera is produced as above. The purified CAP37 isoform is also obtained as above. A sandwich ELISA uses the mouse monoclonal antibody as a capture antibody and the rabbit antiserum as a detection antibody (as described elsewhere herein). A standard curve can include the purified CAP37 isoform in a dose range from 0-200 ng/ml, for example. The patients' plasma is added undiluted or diluted at 1:4, for example, and the ELISA is developed according to standard protocols. The amount of CAP37 isoform present in the patients sample is determined from the values obtained on the standard curve.

By purifying the CAP37 isoform and making antibodies that are specific to this large molecular weight band, the test is specific for this isoform and does not detect the neutrophil-derived CAP37 protein which is found at a molecular weight range of 29-37kDa. As used herein, the "affinity" of an antibody for a CAP37 isoform is characterized by its $K_d$, or disassociation constant. A stronger affinity is represented by a lower $K_d$ while a weaker affinity is represented by a higher $K_d$. As such, an antibody of the present invention preferably has an affinity for its corresponding antigen represented by a $K_d \leq 100$ nM, or $\leq 50$ nM, or more preferably by a $K_d \leq 25$ nM, and still more preferably by a $K_d \leq 10$ nM, and even more preferably by a $K_d \leq 5$ nM.

All references, articles and patents cited herein are hereby incorporated herein in their entirety by reference.

Changes may be made in the various compositions, methods, components, kits, and assemblies described herein or in the steps or the sequence of steps of the methods described herein without departing from the spirit and scope of the invention as described herein.

Cited References:

1. Shafer W M, Martin L E, Spitznagel 3K: Cationic antimicrobial proteins isolated from human neutrophil granulocytes in the presence of diisopropyl fluorophosphate. Infect Immun 1984, 45:29-35.

2. Pereira H A, Spitznagel J K, Pohl J, Wilson D E, Morgan J, Palings I, Larrick J W: CAP37, a 37 kD human neutrophil granule cationic protein shares homology with inflammatory proteinases. Life Sciences 1990, 46:189-196.

3. Pohl J, Pereira H A, Martin N M, Spitznagel J K: Amino acid sequence of CAP37, a human neutrophil granule-derived antibacterial and monocyte-specific chemotactic glycoprotein structurally similar to neutrophil elastase. FEBS Letters 1990, 272:200-204.

4. Shafer W M, Martin L E, Spitznagel J K: Late intraphagosomal hydrogen ion concentration favors the in vitro antimicrobial capacity of a 37-kilodalton cationic granule protein of human neutrophil granules. Infect Immun 1986, 53:651-655.

5. Brackett D J, Lerner M R, Lacquement M A, He R, Pereira H A: A synthetic lipopolysaccharide-binding peptide based on the neutrophil-derived protein CAP37 prevents endotoxin-induced responses in conscious rats. Infect Immun 1997, 65:2803-2811.

6. Pereira H A, Shafer W M, Pohl J, Martin L E, Spitznagel J K: CAP37, a human neutrophil-derived chemotactic factor with monocyte specific activity. J Clin Invest 1990, 85:1468-1476.

7. Østergaard E, Flodgaard H: A neutrophil-derived proteolytic inactive elastase homologue (hHBP) mediates reversible contraction of fibroblasts and endothelial cell monolayers and stimulates monocyte survival and thrombospondin secretion. J Leukoc Biol 1992, 51:316-323.

8. Heinzelmann M, Mercer-Jones M A, Flodgaard H, Miller F N: Heparin-binding protein (CAP37) is internalized in monocytes and increases LPS-induced monocyte activation. J Immunol 1998, 160:5530-5536.

9. Rasmussen P B, Bjørn S, Hastrup S, Nielsen P F, Norris K, Thim L, Wiberg F C, Flodgaard H: Characterization of recombinant human HBP/CAP37/azurocidin, a pleiotropic mediator of inflammation-enhancing LPS-induced cytokine release from monocytes. FEBS letters 1996, 390:109-112.

10. Heinzelmann M, Platz A, Flodgaard H, Polk Jr H C, Miller F N: Endocytosis of heparin-binding protein (CAP37) is essential for the enhancement of lipopolysaccharide-induced TNF-α production in human monocytes. J Immunol 1999, 162:4240-4245.

11. Pereira H A, Moore P, Grammas P: CAP37, a neutrophil granule-derived protein stimulates protein kinase C activity in endothelial cells. J Leukoc Biol 1996 a, 60:415-422.

12. Olofsson A M, Vestberg M, Herwald H, Rygaard J, David G, Arfors K-E, Linde V, Flodgaard H, Dedio J, Müller-Esterl W, Lundgren-Åkerlund E: Heparin-binding protein targeted to mitochondrial compartments protects endothelial cells from apoptosis. J Clin Invest 1999, 104:885-894.

13. Pereira H A, Kumar P, Grammas P: Expression of CAP37, a novel inflammatory mediator, in Alzheimer's disease. Neurobiol Aging 1996 b, 17:753-759.

14. Ross R: Atherosclerosis—an inflammatory disease. N Engl J Med 1999, 340:115-126.

15. Akiyama H, Barger S, Barnum S, Bradt B, Bauer J, Cole G M, Cooper N R, Eikelenboom P, Emmerling M, Fiebich B L, Finch C E, Frautschy S, Griffin W S T, Hampel H, Hull M, Landreth G, Lue L-F, Mrak R, Mackenzie I R, McGeer P L, O'Banion K, Pachter J, Pasinetti G, Plata-Salaman C, Rogers J, Rydel R, Shen Y, Streit W, Strohmeyer R, Tooyoma I, Van Muiswinkel F L, Veerhuis R, Walker D, Webster S, Wegrzyniak B, Wenk G, Wyss-Coray T: Inflammation and Alzheimer's disease. Neurobiol Aging 2000, 21:383-421.

16. Diglio C A, Grammas P, Giacomelli F, Wiener J: Angiogenesis in rat aorta ring explant cultures. Lab Invest 1989, 60:523-531.

17. Jaffe A E, Nachman R L, Becker C G, Minick C R: Culture of human endothelial cells derived from umbilical veins. J Clin Invest 1973, 52:2745-2756.

18. Grabner R, Till U, Heller R: Flow cytometric determination of E-selectin, vascular cell adhesion molecule-1, and intercellular cell adhesion molecule-1 in formaldehyde-fixed endothelial monolayers. Cytometry 2000, 40:238-244.

19. Chomczynski P, Sacchi N: Single-step method of RNA isolation by acid guanidinium thiocyanate-phenol-chloroform extraction. Anal Biochem 1987, 162:156-159.

20. Corpet F: Multiple sequence alignment with hierarchical clustering. Nucl Acids Res 1988, 16:10881-10890.

21. Morgan J G, Sukiennicki T, Pereira H A, Spitznagel J K, Guerra M E, Larrick J W: Cloning of the cDNA for the serine protease homolog CAP37/Azurocidin, a microbicidal and chemotactic protein from human granulocytes. J Immunol 1991, 147:3210-3214.

22. Pereira H A, Erdem I, Pohl J, Spitznagel J K: Synthetic bactericidal peptide based on CAP37: a 37-kDa human neutrophil granule-associated cationic antimicrobial protein chemotactic for monocytes. Proc Natl Acad Sci (USA) 1993, 90:4733-4737.

23. Enk C D, Mahanty S, Blauvelt A, Katz S I: UVB induces IL-12 transcription in human keratinocytes in vivo and in vitro. Photochem Photobio 1996, 63:854-859.

24. Walter M J, Kajiwara N, Karanja P, Castro M, Holtzman M J: Interleukin 12 p40 production by barrier epithelial cells during airway inflammation. J Exp Med 2001, 193:339-351.

25. Lonnemann G, Endres S, Van der Meer J W M, Cannon J G, Koch K M, Dinarello C A: Differences in the synthesis and kinetics of release of interleukin 1 alpha, interleukin 1 beta and tumor necrosis factor from human mononuclear cells. Eur J Immunol 1989, 19:1531-1536.

26. Sears P, Wong C-H: Enzyme action in glycoprotein synthesis. Cell Mol Life Sci 1998, 54:223-252.

27. Flodgaard H, Østergaard E, Bayne S, Svendsen A, Thomsen J, Engels M, Wollmer A: Covalent structure of two novel neutrophile leucocyte-derived proteins of porcine and human origin: neutrophil elastase homologues with strong monocyte and fibroblast chemotactic activities. Eur J Biochem 1991, 197:535-547.

28. Gautam N, Olofsson A M, Herwald H, Iversen L F, Lundgren-Akerlund E, Hedqvist P, Arfors K-E, Flodgaard H, Lindbom L: Heparin-binding protein (HBP/CAP37): A missing link in neutrophil-evoked alteration of vascular permeability. Nat Med 2001, 7:1123-1127.

29. Grammas P: A damaged microcirculation contributes to neuronal cell death in Alzheimer's disease. Neurobiol Aging 2000, 21:199-205.

30. Pereira H. A., Martin, L E, and Spitznagel, J K: Quantitation of a cationic antimicrobial granule protein of human polymorphonuclear leukocytes by ELISA. J. Immunol. Meth., 1989, 117:115-120.

What is claimed is:

1. A method of detecting in a subject, a chronic inflammatory-associated disease selected from the group consisting of osteoarthritis and atherosclerosis, comprising:

analyzing a sample of at least one of serum and plasma obtained from the subject to isolate and measure an amount of an isoform of endothelial CAP37 protein in the sample, wherein the isoform of endothelial CAP37 protein has an apparent molecular weight of about 135 kDa ±15 kDa as assessed by SDS PAGE under reducing conditions, wherein the isoform of endothelial CAP37 protein is isolated by binding to monoclonal antibody D5F10, and wherein the subject does not have an active acute infection; and correlating the presence of the isoform of endothelial CAP37 protein with the presence of the chronic inflammatory-associated disease selected from the group consisting of osteoarthritis and atherosclerosis in the subject when the isoform of endothelial CAP37 protein is present in an amount which is at least twice an amount of the isoform calculated as an average of said isoform found in a control population.

2. The method of claim 1 comprising detecting osteoarthritis in the subject.

3. The method of claim 1 comprising detecting atherosclerosis in the subject.

4. A method of detecting in a subject, a chronic inflammatory-associated disease selected from the group consisting of osteoarthritis and atherosclerosis in a subject, comprising:

isolating an isoform of endothelial CAP37 protein from a sample of at least one of serum or plasma obtained from the subject, wherein the isoform of endothelial CAP37 protein has an apparent molecular weight of about 135 kDa ±15 kDa as assessed by SDS PAGE under reducing conditions, wherein the isoform of endothelial CAP37 protein is isolated by binding to monoclonal antibody D5F10, and wherein the subject does not have an active acute infection; and comparing the measurement of the amount of said isoform of endothelial CAP37 protein in the sample to an amount calculated as an average of said isoform found in a control population, and wherein, when the measurement of the amount of said isoform of endothelial CAP37 protein obtained from the subject is at least twice the amount calculated as an average of said isoform found in a control population, the subject is determined to have at least one of osteoarthritis and atherosclerosis.

5. The method of claim 4 comprising detecting osteoarthritis in the subject.

6. The method of claim 4 comprising detecting atherosclerosis in the subject.

7. A method of detecting atherosclerosis in a subject, comprising:

obtaining a measurement of an amount of an isoform of endothelial CAP37 protein in a sample of at least one of serum or plasma obtained from the subject, wherein the isoform of endothelial CAP37 protein has an apparent molecular weight of about 135 kDa ±15 kDa as assessed by SDS PAGE under reducing conditions, wherein the isoform of endothelial CAP37 protein is isolated by binding to monoclonal antibody D5F10, and wherein the subject does not have an active acute infection; and comparing the measurement of the amount of said isoform of endothelial CAP37 protein in the sample to an amount calculated as an average of said isoform found in a control population, and wherein, when the measurement of the amount of said isoform of endothelial CAP37 protein obtained from the subject is at least twice the amount calculated as an average of said isoform found in a control population, the subject is determined to have atherosclerosis.

* * * * *

UNITED STATES PATENT AND TRADEMARK OFFICE
CERTIFICATE OF CORRECTION

PATENT NO. : 8,450,071 B2  
APPLICATION NO. : 12/904917  
DATED : May 28, 2013  
INVENTOR(S) : Heloise Anne Pereira Page 1 of 1

It is certified that error appears in the above-identified patent and that said Letters Patent is hereby corrected as shown below:

In the Specifications:

Column 10, line 15: Delete "octyiglucoside" and replace with -- octylglucoside --

Column 21, line 62: Delete "3K:" and replace with -- JK: --

Signed and Sealed this  
Twenty-third Day of July, 2013

Teresa Stanek Rea  
*Acting Director of the United States Patent and Trademark Office*

UNITED STATES PATENT AND TRADEMARK OFFICE
CERTIFICATE OF CORRECTION

| | |
|---|---|
| PATENT NO. | : 8,450,071 B2 |
| APPLICATION NO. | : 12/904917 |
| DATED | : May 28, 2013 |
| INVENTOR(S) | : Heloise Anne Pereira |

It is certified that error appears in the above-identified patent and that said Letters Patent is hereby corrected as shown below:

In the Specification

Column 1, Lines 20-23: Delete entirety of paragraph and replace with -- This invention was made with government support under Grant AI028018 awarded by the National Institutes of Health. The government has certain rights in the invention. --

Signed and Sealed this
Fourteenth Day of December, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: Completely synthesized

<400> SEQUENCE: 1
gtgctgggtg cctatgacct gagg                                          24

<210> SEQ ID NO 2
<211> LENGTH: 23
<212> TYPE: DNA
<213> ORGANISM: Artificial sequence
<220> FEATURE:
<223> OTHER INFORMATION: Completely synthesized

<400> SEQUENCE: 2
aagagcgcca ctcgggtgaa gaa                                           23

<210> SEQ ID NO 3
<211> LENGTH: 24
<212> TYPE: DNA
<213> ORGANISM: Artificial sequence
<220> FEATURE:
<223> OTHER INFORMATION: Completely synthesized

<400> SEQUENCE: 3
cagaatcaag gcaggcactt ctgc                                          24

<210> SEQ ID NO 4
<211> LENGTH: 24
<212> TYPE: DNA
<213> ORGANISM: Artificial sequence
```

```
<220> FEATURE:
<223> OTHER INFORMATION: Completely synthesized

<400> SEQUENCE: 4
gagaacacca tcgatccagt ctcg                                              24

<210> SEQ ID NO 5
<211> LENGTH: 24
<212> TYPE: DNA
<213> ORGANISM: Artificial sequence
<220> FEATURE:
<223> OTHER INFORMATION: Completely synthesized

<400> SEQUENCE: 5
ctgcagaggc agtggcagta tcgt                                              24

<210> SEQ ID NO 6
<211> LENGTH: 24
<212> TYPE: DNA
<213> ORGANISM: Artificial sequence
<220> FEATURE:
<223> OTHER INFORMATION: Completely synthesized

<400> SEQUENCE: 6
gcagaagtgc ctgccttgat tctg                                              24

<210> SEQ ID NO 7
<211> LENGTH: 24
<212> TYPE: DNA
<213> ORGANISM: Artificial sequence
<220> FEATURE:
<223> OTHER INFORMATION: Completely synthesized

<400> SEQUENCE: 7
cgagactgga tcgatggtgt tctc                                              24

<210> SEQ ID NO 8
<211> LENGTH: 199
<212> TYPE: PRT
<213> ORGANISM: Homo sapiens

<400> SEQUENCE: 8

Gln Asn Gln Gly Arg His Phe Cys Gly Gly Ala Leu Ile His Ala Arg
1               5                   10                  15

Phe Val Met Thr Ala Ala Ser Cys Phe Gln Ser Gln Asn Pro Gly Val
            20                  25                  30

Ser Thr Val Val Leu Gly Ala Tyr Asp Leu Arg Arg Arg Glu Arg Gln
        35                  40                  45

Ser Arg Gln Thr Phe Ser Ile Ser Ser Met Ser Glu Asn Gly Tyr Asp
    50                  55                  60

Pro Gln Gln Asn Leu Asn Asp Leu Met Leu Leu Gln Leu Asp Arg Glu
65                  70                  75                  80

Ala Asn Leu Thr Ser Ser Val Thr Ile Leu Pro Leu Pro Leu Gln Asn
                85                  90                  95

Ala Thr Val Glu Ala Gly Thr Arg Cys Gln Val Ala Gly Trp Gly Ser
            100                 105                 110

Gln Arg Ser Gly Gly Arg Leu Ser Arg Phe Pro Arg Phe Val Asn Val
        115                 120                 125

Thr Val Thr Pro Glu Asp Gln Cys Arg Pro Asn Asn Val Cys Thr Gly
    130                 135                 140

Val Leu Thr Arg Arg Gly Gly Ile Cys Asn Gly Asp Gly Gly Thr Pro
145                 150                 155                 160
```

```
Leu Val Cys Glu Gly Leu Ala His Gly Val Ala Ser Phe Ser Leu Gly
                165                 170                 175

Pro Cys Gly Arg Gly Pro Asp Phe Phe Thr Arg Val Ala Leu Phe Arg
            180                 185                 190

Asp Trp Ile Asp Gly Val Leu
        195

<210> SEQ ID NO 9
<211> LENGTH: 597
<212> TYPE: DNA
<213> ORGANISM: Homo sapiens

<400> SEQUENCE: 9
cagaatcaag gcaggcactt ctgcggggt gccctgatcc atgcccgctt cgtgatgacc        60
gcggccagct gcttccaaag ccagaacccc ggggttagca ccgtggtgct gggtgcctat     120
gacctgaggc ggcgggagag gcagtcccgc cagacgtttt ccatcagcag catgagcgag     180
aatggctacg accccagca gaacctgaac gacctgatgc tgcttcagct ggaccgtgag     240
gccaacctca ccagcagcgt gacgatactg ccactgcctc tgcagaacgc cacggtggaa     300
gccggcacca gatgccaggt ggccggctgg gggagccagc gcagtggggg gcgtctctcc     360
cgttttccca ggtttgtcaa cgtgactgtg accccgagg accagtgtcg ccccaacaac     420
gtgtgcaccg gtgtgctcac ccgccgcggt ggcatctgca atggggacgg gggcaccccc     480
ctcgtctgcg agggcctggc ccacggcgtg gcctccttt ccctggggcc ctgtggccga     540
ggccctgact tcttcacccg agtggcgctc ttccgagact ggatcgatgg tgttctc       597
```